(12) United States Patent
Armer et al.

(10) Patent No.: US 7,999,119 B2
(45) Date of Patent: Aug. 16, 2011

(54) COMPOUNDS HAVING CRTH2 ANTAGONIST ACTIVITY

(75) Inventors: Richard Edward Armer, Cambridge (GB); Graham Michael Wynne, Bicester (GB); Colin Richard Dorgan, Abingdon (GB); Peter David Johnson, Oxford (GB)

(73) Assignee: Oxagen Limited, Oxon (GB)

( * ) Notice: Subject to any disclaimer, the term of this patent is extended or adjusted under 35 U.S.C. 154(b) by 135 days.

(21) Appl. No.: 12/374,702

(22) PCT Filed: Jul. 20, 2007

(86) PCT No.: PCT/GB2007/002761
§ 371 (c)(1),
(2), (4) Date: Sep. 23, 2009

(87) PCT Pub. No.: WO2008/012511
PCT Pub. Date: Jan. 31, 2008

(65) Prior Publication Data
US 2010/0035956 A1 Feb. 11, 2010

(30) Foreign Application Priority Data

Jul. 22, 2006 (GB) .................................. 0614608.8
Dec. 4, 2006 (GB) .................................. 0624176.4

(51) Int. Cl.
*C07D 209/04* (2006.01)
*A61K 31/40* (2006.01)
(52) U.S. Cl. ....................................... 548/510; 514/416
(58) Field of Classification Search .................. 548/510; 514/416
See application file for complete search history.

(56) References Cited

U.S. PATENT DOCUMENTS

| 5,641,800 | A | 6/1997 | Bach et al. |
| 6,214,991 | B1 | 4/2001 | Jones et al. |
| 7,582,672 | B2 | 9/2009 | Middlemiss et al. |
| 7,750,027 | B2 | 7/2010 | Armer et al. |
| 2009/0018138 | A1 | 1/2009 | Middlemiss et al. |
| 2009/0018139 | A1 | 1/2009 | Middlemiss et al. |
| 2009/0018338 | A1 | 1/2009 | Middlemiss et al. |
| 2009/0023788 | A1 | 1/2009 | Middlemiss et al. |
| 2009/0192195 | A1 | 7/2009 | Armer et al. |
| 2010/0022613 | A1 | 1/2010 | Armer et al. |
| 2010/0041699 | A1 | 2/2010 | Boyd et al. |
| 2010/0266535 | A1 | 10/2010 | Armer et al. |
| 2010/0330077 | A1 | 12/2010 | Armer et al. |

FOREIGN PATENT DOCUMENTS

| EP | 1 505 061 A1 | 2/2005 |
| WO | WO 2005/044260 A1 | 5/2005 |
| WO | WO 2009/077728 A1 | 6/2009 |

OTHER PUBLICATIONS

Unpublished U.S. Appl. No. 12/779,638, filed May 13, 2010; inventors: Hunter et al., U.S. Patent and Trademark Office, Alexandria, Virginia.
Unpublished U.S. Appl. No. 13/014,314, filed Jan. 26, 2011; inventors: Armer et al., U.S. Patent and Trademark Office, Alexandria, Virginia.
Unpublished U.S. Appl. No. 13/017,860, filed Jan. 31, 2011; inventors: Armer et al., U.S. Patent and Trademark Office, Alexandria, Virginia.

*Primary Examiner* — Robert Havlin
(74) *Attorney, Agent, or Firm* — Sterne, Kessler, Goldstein & Fox P.L.L.C.

(57) ABSTRACT

Compounds of general formula (I) wherein R is phenyl optionally substituted with one or more halo substituents; and their pharmaceutically acceptable salts, hydrates, solvates, complexes or prodrugs are useful in orally administrable compositions for the treatment of allergic diseases such as asthma, allergic rhinitis and atopic dermatitis.

10 Claims, 5 Drawing Sheets

COMPOUNDS HAVING CRTH2 ANTAGONIST ACTIVITY

The present invention relates to compounds which are useful as pharmaceuticals, to methods for preparing these compounds, compositions containing them and their use in the treatment and prevention of allergic diseases such as asthma, allergic rhinitis and atopic dermatitis and other inflammatory diseases mediated by prostaglandin $D_2$ ($PGD_2$) or other agonists acting at the CRTH2 receptor on cells including eosinophils, basophils and Th2 lymphocytes.

$PGD_2$ is an eicosanoid, a class of chemical mediator synthesised by cells in response to local tissue damage, normal stimuli or hormonal stimuli or via cellular activation pathways. Eicosanoids bind to specific cell surface receptors on a wide variety of tissues throughout the body and mediate various effects in these tissues. $PGD_2$ is known to be produced by mast cells, macrophages and Th2 lymphocytes and has been detected in high concentrations in the airways of asthmatic patients challenged with antigen (Murray et al, (1986), *N. Engl. J. Med.* 315: 800-804). Instillation of $PGD_2$ into airways can provoke many features of the asthmatic response including bronchoconstriction (Hardy et al, (1984) *N. Engl. J. Med.* 311: 209-213; Sampson et al, (1997) *Thorax* 52: 513-518) and eosinophil accumulation (Emery et al, (1989) *J. Appl. Physiol.* 67: 959-962).

The potential of exogenously applied $PGD_2$ to induce inflammatory responses has been confirmed by the use of transgenic mice overexpressing human $PGD_2$ synthase which exhibit exaggerated eosinophilic lung inflammation and Th2 cytokine production in response to antigen (Fujitani et al, (2002) *J. Immunol.* 168: 443-449).

The first receptor specific for $PGD_2$ to be discovered was the DP receptor which is linked to elevation of the intracellular levels of cAMP. However, $PGD_2$ is thought to mediate much of its proinflammatory activity through interaction with a G protein-coupled receptor termed CRTH2 (chemoattractant receptor-homologous molecule expressed on Th2 cells) which is expressed by Th2 lymphocytes, eosinophils and basophils (Hirai et al, (2001) *J. Exp. Med.* 193: 255-261, and EP0851030 and EP-A-1211513 and Bauer et al, EP-A-1170594). It seems clear that the effect of $PGD_2$ on the activation of Th2 lymphocytes and eosinophils is mediated through CRTH2 since the selective CRTH2 agonists 13,14 dihydro-15-keto-$PGD_2$ (DK-$PGD_2$) and 15R-methyl-$PGD_2$ can elicit this response and the effects of $PGD_2$ are blocked by an anti-CRTH2 antibody (Hirai et al, 2001; Monneret et al, (2003) *J. Pharmacol. Exp. Ther.* 304: 349-355). In contrast, the selective DP agonist BW245C does not promote migration of Th2 lymphocytes or eosinophils (Hirai et al, 2001; Gervais et al, (2001) *J. Allergy Clin. Immunol.* 108: 982-988). Based on this evidence, antagonising $PGD_2$ at the CRTH2 receptor is an attractive approach to treat the inflammatory component of Th2-dependent allergic diseases such as asthma, allergic rhinitis and atopic dermatitis.

EP-A-1170594 suggests that the method to which it relates can be used to identify compounds which are of use in the treatment of allergic asthma, atopic dermatitis, allergic rhinitis, autoimmune, reperfusion injury and a number of inflammatory conditions, all of which are mediated by the action of $PGD_2$ or other agonists at the CRTH2 receptor.

Compounds which bind to CRTH2 are taught in WO-A-03066046 and WO-A-03066047. These compounds are not new but were first disclosed, along with similar compounds, in GB 1356834, GB 1407658 and GB 1460348, where they were said to have anti-inflammatory, analgesic and anti-pyretic activity. WO-A-03066046 and WO-A-03066047 teach that the compounds to which they relate are modulators of CRTH2 receptor activity and are therefore of use in the treatment or prevention of obstructive airway diseases such as asthma, chronic obstructive pulmonary disease (COPD) and a number of other diseases including various conditions of bones and joints, skin and eyes, GI tract, central and peripheral nervous system and other tissues as well as allograft rejection. These compounds are all indole derivatives with an acetic acid substituent at the 3-position of the indole ring.

PL 65781 and JP 43-24418 also relate to indole-3 acetic acid derivatives which are similar in structure to indomethacin and, like indomethacin, are said to have anti-inflammatory and antipyretic activity. Thus, although this may not have been appreciated at the time when these documents were published, the compounds they describe are COX inhibitors, an activity which is quite different from that of the compounds of the present invention. Indeed, COX inhibitors are contraindicated in the treatment of many of the diseases and conditions, for example asthma and inflammatory bowel disease for which the compounds of the present invention are useful, although they may sometimes be used to treat arthritic conditions.

There is further prior art which relates to indole-1-acetic acid compounds, although these are not described as CRTH2 antagonists. For example WO-A-9950268, WO-A-0032180, WO-A-0151849 and WO-A-0164205 all relate to compounds which are indole-1-acetic acid derivatives but these compounds are said to be aldose reductase inhibitors useful in the treatment of diabetes mellitus (WO-A-9950268, WO-A-0032180 and WO-A-0164205) or hypouricemic agents (WO-A-0151849). There is no suggestion in any of these documents that the compounds would be useful for the treatment of diseases and conditions mediated by $PGD_2$ or other CRTH2 receptor agonists.

U.S. Pat. No. 4,363,912 relates to indole-1-acetic acid derivatives which are said to be inhibitors of thromboxane synthetase and to be useful in the treatment of conditions such as thrombosis, ischaemic heart disease and stroke.

WO-A-9603376 relates to compounds which are said to be $sPLA_2$ inhibitors which are useful in the treatment of bronchial asthma and allergic rhinitis. These compounds all have amide or hydrazide substituents in place of the carboxylic acid derivative of the compounds of the present invention.

JP 2001247570 relates to a method of producing a 3-benzothiazolylmethyl indole acetic acid, which is said to be an aldose reductase inhibitor.

U.S. Pat. No. 4,859,692 relates to compounds which are said to be leukotriene antagonists useful in the treatment of conditions such as asthma, hay fever and allergic rhinitis as well as certain inflammatory conditions such as bronchitis, atopic and ectopic eczema. Some of the compounds of this document are indole-1-acetic acids but the same authors, in *J. Med. Chem.*, 6(33), 1781-1790 (1990), teach that compounds with an acetic acid group on the indole nitrogen do not have significant peptidoleukotriene activity. In view of this, it is most surprising that the compounds of the present invention, which all have an acetic acid group on the indole nitrogen, are useful for treating conditions such as asthma, hay fever and allergic rhinitis.

U.S. Pat. No. 4,273,782 is directed to indole-1-acetic acid derivatives which are said to be useful in the treatment of conditions such as thrombosis, ischaemic heart disease, stroke, transient ischaemic attack, migraine and the vascular complications of diabetes. There is no mention in the document of conditions mediated by the action of $PGD_2$ or other agonists at the CRTH2 receptor.

U.S. Pat. No. 3,557,142 relates to 3-substituted-1-indole carboxylic acids and esters which are said to be useful in the treatment of inflammatory conditions.

WO-A-03/097598 relates to compounds which are CRTH2 receptor antagonists. They do not have an aromatic substituent at the indole-3 position.

Cross et al, *J. Med. Chem.* 29, 342-346 (1986) relates to a process for preparing indole-1-acetic acid derivatives from the corresponding esters. The compounds to which it relates are said to be inhibitors of thromboxane synthetase.

EP-A-0539117 relates to indole-1-acetic acid derivatives which are leukotriene antagonists US 2003/0153751 relates to indole-1-acetic acid derivatives which are sPLA$_2$ inhibitors. However, all of the exemplified compounds have bulky substituents at the 2- and 5-positions of the indole system and are therefore very different from the compounds of the present invention.

US 2004/011648 discloses indole-1-acetic acid derivatives which are inhibitors of PAI-1. There is no suggestion that the compounds might have CRTH2 antagonist activity.

WO 2004/058164 relates to compounds which are said to be asthma and allergic inflammation modulators. The only compounds for which activity is demonstrated are entirely different in structure from the indole-1-acetic acid derivatives of the present invention.

Compounds which bind to the CRTH2 receptor are disclosed in WO-A-03/097042 and WO-A-03/097598. These compounds are indole acetic acids but in WO-A-03/097042 the indole system is fused at the 2-3 positions to a 5-7 membered carbocyclic ring. In WO-A-03/097598 there is a pyrrolidine group at the indole 3-position.

WO-A-03/101981, WO-A-03/101961 and WO-A-2004/007451 all relate to indole-1-acetic acid derivatives which are said to be CRTH2 antagonists but which differ in structure from the compounds of general formula (I) because there is no spacer or an —S— or —SO$_2$— group at to the indole 3-position in place of the CH$_2$ group of the compounds of the present invention as described below.

WO-A-2005/019171 also describes indole-1-acetic acid derivatives which are said to be CRTH2 antagonists and which are said to be useful for the treatment of various respiratory diseases. These compounds all have a substituent which is linked to the indole-3 position by an oxygen spacer.

WO-A-2005/094816 again describes indole-1-acetic acid compounds, this time with an aliphatic substituent at the 3-position of the indole ring. The compounds are said to be CRTH2 antagonists.

WO-A-2006/034419 relates to CRTH2 antagonist indole compounds which have a heterocyclic or heteroaromatic substituent directly linked to the 3-position of the indole ring system.

In our earlier application, WO-A-2005/044260, we describe compounds which are antagonists of PGD$_2$ at the CRTH2 receptor. These compounds are indole-1-acetic acid derivatives substituted at the 3-position with a group CR$^8$R$^9$, wherein R$^9$ is hydrogen or alkyl and R$^8$ is an aromatic moiety which may be substituted with one or more substituents. The compounds described in this document are potent antagonists in vitro of PGD$_2$ at the CRTH2 receptor. However, we have found that when tested in vivo, the pharmacokinetic profile of some compounds is not optimal and their potency in the whole blood eosinophil shape change test, which gives an indication of the likely in vivo activity of the compounds, is often somewhat less than might have been expected from the in vitro binding results.

Surprisingly, however, we have found that by making changes to the R$^8$ group of the compounds of WO-A-2005/ 044260 we are able to achieve improvements in the in vitro whole blood eosinophil shape change potency and the in vivo inhibition of DK-PGD$_2$-induced blood eosinophilia and the pharmacokinetic profile on oral administration to a subject.

The present invention therefore relates to novel compounds which bind to CRTH2 and which are therefore useful in the treatment of diseases and conditions mediated by the activity of PGD$_2$ at the CRTH2 receptor.

In the present invention there is provided a compound of general formula (I)

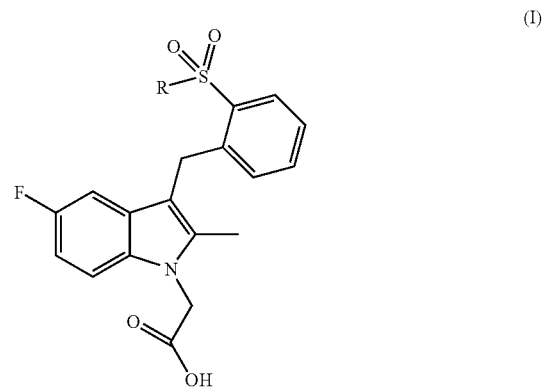

(I)

wherein R is phenyl optionally substituted with one or more halo substituents;

or a pharmaceutically acceptable salt, hydrate, solvate, complex or prodrug thereof.

The compounds of general formula (I) are antagonists at the CRTH2 receptor and are useful in the treatment of conditions which are mediated by PGD$_2$ or other agonists binding to CRTH2. These include allergic diseases, asthmatic conditions and inflammatory diseases, examples of which are asthma, including allergic asthma, bronchial asthma, exacerbations of asthma and related allergic diseases caused by viral infection, particularly those exacerbations caused by rhinovirus and respiratory syncytial virus intrinsic, extrinsic, exercise-induced, drug-induced and dust-induced asthma, treatment of cough, including chronic cough associated with inflammatory and secretory conditions of the airways and iatrogenic cough, acute and chronic rhinitis, including rhinitis medicamentosa, vasomotor rhinitis, perennial allergic rhinitis, seasonal allergic rhinitis, nasal polyposis, acute viral infection including common cold, infection due to respiratory syncytial virus, influenza, coronavirus and adenovirus, atopic dermatitis, contact hypersensitivity (including contact dermatitis), eczematous dermatitis, phyto dermatitis, photo dermatitis, sebhorroeic dermatitis, dermatitis herpetiformis, lichen planus, lichen sclerosis et atrophica, pyoderma gangrenosum, skin sarcoid, discoid lupus erythematosus, pemphigus, pemphigoid, epidermolysis bullosa urticaria, angioedema, vasculitides, toxic erythemas, cutaneous eosinophilias, alopecia areata, male-pattern baldness, Sweet's syndrome, Weber-Christian syndrome, erythema multiforme, cellulitis, panniculitis, cutaneous lymphomas, non-melanoma skin cancer and other dysplastic lesions; blepharitis conjunctivitis, especially allergic conjunctivitis, anterior and posterior uveitis, choroiditis, autoimmune, degenerative or inflammatory disorders affecting the retina, ophthalmitis; bronchitis, including infectious and eosinophilic bronchitis, emphysema, bronchiectasis, farmer's lung, hypersensitivity pneumonitis, idiopathic interstitial pneumonias, complications of lung transplantation, vasculitic and thrombotic disorders of the lung vasculature, pulmonary hypertension, food allergies, gingivitis, glossitis, periodontitis, oesophagitis including reflux, eosinophilic gastroenteritis, proctitis, pruris ani, celiac disease, food-related allergies, inflammatory bowel disease, ulcerative colitis and Crohn's disease, mastocytosis and also other CRTH2-mediated diseases, for example autoimmune diseases such as hyper IgE syndrome, Hashimoto's thyroiditis, Graves' disease, Addison's disease, diabetes mellitus, idiopathic thrombocytopaenic purpura, eosinophilic paschiitis, antiphospholipid syndrome and systemic lupus erythematosus, AIDS, leprosy, Sezary syndrome, paraneoplastic syndrome, mixed and undifferentiated connective tissue diseases, inflammatory myopathies including dermatomyositis and polymyositis, polymalgia rheumatica, juvenile arthritis, rheumatic fever, vasculitides including giant cell arteritis, Takayasu's arteritis, Churg-Strauss syndrome, polyarteritis nodosa, microscopic polyarteritis, temporal arteritis, myasthenia gravic, acute and chronic pain, neuropathic pain syndromes, neurodegeneration, central and peripheral nervous system complications of malignant, infectious or autoimmune processes, low back pain, familial Mediterranean Fever, Muckle-Wells syndrome, Familial Hibernian fever, Kikuchi disease, psoriasis, acne, multiple sclerosis, allograft rejection, reperfusion injury, chronic obstructive pulmonary disease, as well as rheumatoid arthritis, Still's disease, ankylosing spondylitis, reactive arthritis, undifferentiated spondarthropathy, psoriatic arthritis, septic arthritis and other infection-related arthopathies and bone disorders and osteoarthritis; acute and chronic crystal-induced synovitis including urate gout, calcium pyrophosphate deposition disease, calcium paptite related tendon syndrome and synovial inflammation, Behcet's disease, primary and secondary Sjogren's syndrome systemic sclerosis and limited scleroderma; hepatitis, cirrhosis of the liver, cholecystitis, pancreatitis, nephritis, nephritic syndrome, cystitis and Hunner's ulcer, acute and chronic urethritis, prostatitis, epididymitis, oophoritis, salpingitis, vulvo-vaginitis, Peyronie's disease, erectile dysfunction, Alzheimer's disease and other dementing disorders; pericarditis, myocarditis, inflammatory and auto-immune cardiomyopathies including myocardial sarcoid, ischaemic reperfusion injuries, endocarditis, valvulitis, aortitis, phlebitis, thrombosis, treatment of common cancers and fibrotic conditions such as idiopathic pulmonary fibrosis including cryptogenic fibrosing alveolitis, keloids, excessive fibrotic scarring/adhesions post surgery, liver fibrosis including that associated with hepatitis B and C, uterine fibroids, sarcoidosis, including neurosarcoidosis, scleroderma, kidney fibrosis resulting from diabetes, fibrosis associated with RA, atherosclerosis, including cerebral atherosclerosis, vasculitis, myocardial fibrosis resulting from myocardial infarction, cystic fibrosis, restenosis, systemic sclerosis, Dupuytren's disease, fibrosis complicating antineoplastic therapy and chronic infection including tuberculosis and aspergillosis and other fungal infections, CNS fibrosis following stroke or the promotion of healing without fibrotic scarring.

The compounds are particularly useful for the treatment or prevention of allergic asthma, perennial allergic rhinitis, seasonal allergic rhinitis, atopic dermatitis, contact hypersensitivity (including contact dermatitis), conjunctivitis, especially allergic conjunctivitis, eosinophilic bronchitis, food allergies, eosinophilic gastroenteritis, inflammatory bowel disease, ulcerative colitis and Crohn's disease, mastocytosis, pain, neurodegenerative diseases and also other $PGD_2$-mediated diseases, for example autoimmune diseases such as hyper IgE syndrome and systemic lupus erythematus, psoriasis, acne, multiple sclerosis, allograft rejection, reperfusion injury, chronic obstructive pulmonary disease, as well as rheumatoid arthritis, psoriatic arthritis and osteoarthritis.

The improved potency in the whole blood eosinophil shape change test and pharmacokinetic profile of the compounds of general formula (I) is particularly surprising since some of the compounds of WO-A-2005/044260, which are close in structure to the compounds of general formula (I) do not have these advantageous properties. In particular, the compound of Example 17 of WO-A-2005/044260 is similar to the compounds of the present invention and might have been expected to have similar properties. However, the replacement of the methylsulfonyl group at the 4-position of the benzene ring in Example 17 of WO-A-2005/044260 with the $SO_2R$ group at the 2-position of the benzene ring in the compounds of formula (I) has a significant effect on the pharmacokinetics and the activity of the compounds because when Compound 17 of WO-A-2005/044260 is administered orally, its pharmacokinetic profile in vivo is less favourable than that of the compounds of general formula (I).

In addition for many of the compounds of WO-A-2005/044260, we have found that their in vitro whole blood eosinophil shape change activity is often less than might have been expected from their in vitro activity as measured by radioligand binding experiments to the CRTH2 receptor.

Furthermore, the improvement in activity is very specific to the group of compounds of general formula (I) as compounds which are even more closely related than those of WO-A-2005/044260 do not have such favourable properties. For example, the analogues of general formula (I) in which the $SO_2R$ group is at the 3- or 4-position of the benzene ring are less active in in vitro whole blood eosinophil shape change tests.

In the present specification "$C_1$-$C_6$ alkyl" refers to a straight or branched saturated hydrocarbon chain having one to six carbon atoms and optionally substituted with one or more halo substituents or with one or more $C_3$-$C_7$ cycloalkyl groups. Examples include methyl, ethyl, n-propyl, isopropyl, t-butyl, n-hexyl, trifluoromethyl, 2-chloroethyl, methylenecyclopropyl, methylenecyclobutyl, methylenecyclobutyl and methylenecyclopentyl.

"$C_1$-$C_4$ alkyl" and "$C_1$-$C_{18}$ alkyl" have similar meanings except that they contain from one to four and from one to eighteen carbon atoms respectively.

$C_3$-$C_7$ cycloalkyl refers to a saturated 3 to 7 membered carbocyclic ring. Examples of such groups include cyclopropyl, cyclobutyl, cyclopentyl and cyclohexyl.

In the present specification, "halo" refers to fluoro, chloro, bromo or iodo.

The terms "aromatic moiety" and "aryl" in the context of the present specification refer to an aromatic ring system having from 5 to 14 ring carbon atoms and containing up to three rings. Examples of aromatic moieties are benzene and naphthalene. Aryl groups may be substituted with one or more substituents chosen from halo, $C_1$-$C_6$ alkyl, $C_1$-$C_6$ alkoxy, a 5-7-membered heterocyclic ring or $SO_2R^9$ where $R^9$ is as defined above.

Appropriate pharmaceutically and veterinarily acceptable salts of the compounds of general formulae (I) and (II) include basic addition salts such as sodium, potassium, calcium, aluminum, zinc, magnesium and other metal salts as well as choline, diethanolamine, ethanolamine, ethyl diamine and other well known basic addition salts.

Where appropriate, pharmaceutically or veterinarily acceptable salts may also include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, pamoate, pectinate, 3-phenylpropionate, picrate, pivalate, proprionate, tartrate, lactobionate, pivolate, camphorate, undecanoate and succinate, organic sulfonic acids such as methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; and inorganic acids such as hydrochloride, hydrobromide, hydroiodide, sulfate, bisulfate, hemisulfate, thiocyanate, persulfate, phosphoric and sulfonic acids.

Salts which are not pharmaceutically or veterinarily acceptable may still be valuable as intermediates.

Prodrugs are any covalently bonded compounds which release the active parent drug according to general formula (I) in vivo. Examples of prodrugs include alkyl esters of the compounds of general formula (I), for example the esters of general formula (II) below.

If a chiral centre or another form of isomeric centre is present in a compound of the present invention, all forms of such isomer or isomers, including enantiomers and diastereoisomers, are intended to be covered herein. Compounds of the invention containing a chiral centre may be used as a racemic mixture, an enantiomerically enriched mixture, or the racemic mixture may be separated using well-known techniques and an individual enantiomer may be used alone.

In the compounds of general formula (I), it is preferred that the phenyl group R is unsubstituted or is substituted with a single halo substituent, usually fluoro or chloro, which is generally at the 4-position of the phenyl group R.

Among the most preferred compounds are the following:
2-{5-Fluoro-2-methyl-3-[2-(phenylsulfonyl)benzyl]-1H-indol-1-yl}acetic acid;
2-{3-[2-(4-chlorophenylsulfonyl)benzyl]-5-fluoro-2-methyl-1H-indol-1-yl}acetic acid;
2-{5-Fluoro-3-[2-(4-fluorophenylsulfonyl)benzyl]-2-methyl-1H-indol-1-yl}acetic acid;
or the $C_1$-$C_6$ alkyl, aryl, $(CH_2)_mOC(=O)C_1$-$C_6$alkyl, $(CH_2)_mN(R^{11})_2$, $CH((CH_2)_mO(C=O)R^{12})_2$ esters of any of the above; wherein
m is 1 or 2;
$R^{11}$ is hydrogen or methyl;
$R^{12}$ is $C_1$-$C_{18}$ alkyl.

In a further aspect of the present invention, there is provided a compound of general formula (II):

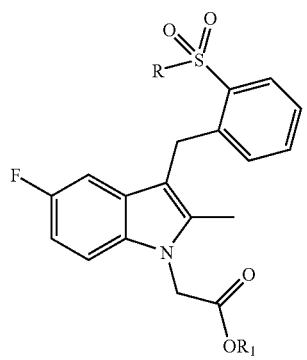

wherein R is as defined for general formula (I); and
$R^1$ is $C_1$-$C_6$ alkyl, aryl, $(CH_2)_mOC(=O)C_1$-$C_6$alkyl, $(CH_2)_mN(R^{11})_2$, $CH((CH_2)_mO(C=O)R^{12})_2$;

m is 1 or 2;
$R^{11}$ is hydrogen or methyl;
$R^{12}$ is $C_1$-$C_{18}$ alkyl.

Compounds of general formula (II) are novel and may be used as prodrugs for compounds of general formula (I). When the compound of general formula (II) acts as a prodrug, it is later transformed to the drug by the action of an esterase in the blood or in a tissue of the patient.

Examples of particularly suitable $R^1$ groups when the compound of general formula (II) is used as a prodrug include: methyl, ethyl, propyl, phenyl, $CH_2OC(=O)tBu$, $CH_2CH_2N(Me)_2$ $CH_2CH_2NH_2$ or $CH(CH_2O(C=O)R^{12})_2$ wherein $R^{12}$ is as defined above.

In addition to their use as prodrugs, compounds of formula (II) wherein $R^1$ is $C_1$-$C_6$ alkyl may be used in a process for the preparation of a compound of general formula (I), the process comprising reacting the compound of general formula (II) with a base such as sodium hydroxide or lithium hydroxide. The reaction may take place in an aqueous solvent or an organic solvent or a mixture of the two. A typical solvent used for the reaction is a mixture of tetrahydrofuran and water.

Compounds of general formula (II) may be prepared from compounds of general formula (III):

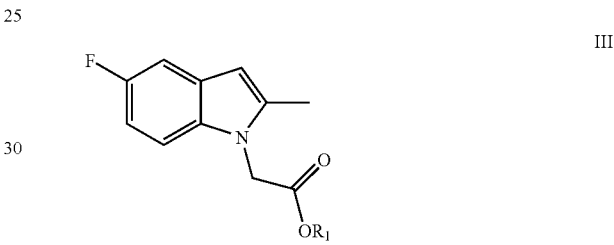

wherein $R^1$ is as defined in general formula (II); by reaction with a compound of general formula (IV):

wherein R is as defined for general formula (I); under acidic reductive alkylation conditions.

Compounds of general formulae (III) are readily available or can be prepared by methods well known to those skilled in the art.

Aldehydes of general formula (IV) can be prepared by deprotecting an acetal of general formula (V)

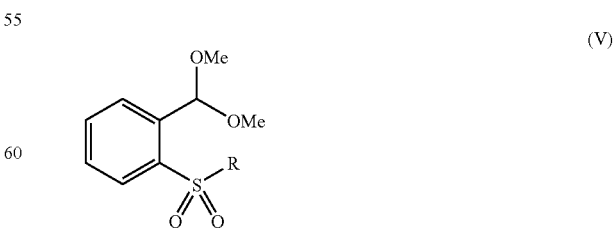

wherein R is as defined for general formula (I). Deprotection may be achieved by reaction with an aqueous acid, for example sulphuric acid, followed by neutralisation with a base, typically solid potassium carbonate. The reaction may be carried out at 0 to 40° C., typically at room temperature.

Compounds of general formula (V) may be prepared by the oxidation of a compound of general formula (VI)

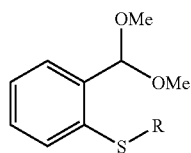

(VI)

wherein R is as defined for general formula (I). The oxidation of the sulfide group can be achieved using an excess amount of an oxidising agent such as chloroperoxybenzoic acid. The reaction mixture may be cooled initially, for example to −5 to 5° C. and then allowed to warm, typically to room temperature.

An acetal of general formula (VI) may be prepared by protecting an aldehyde of general formula (VII)

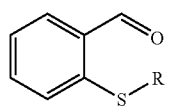

(VII)

wherein R is as defined for general formula (I). The protection may be achieved by reaction with trimethylorthoformate and p-toluene sulfonic acid in dry conditions and under an inert atmosphere followed by sodium methoxide in methanol.

Compounds of general formula (VII) are commercially available. Alternatively, they can be prepared by reacting a compound of general formula (VIII):

R—SH     (VIII)

where R is as defined for general formula (I) with 2-fluorobenzaldehyde. The reaction may be carried out under mildly basic conditions in a polar solvent such as DMSO and under an inert atmosphere at a temperature of from 80 to 110° C.

Compounds of general formula (VIII) are commercially available or may be prepared by methods well known to those of skill in the art.

Another route to compounds of general formula (VII) as defined above is via the formylation of a compound of general formula (X):

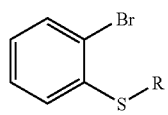

(X)

where R is as defined for general formula (I);
using n-butyl lithium and dimethylformamide (DMF) in an organic solvent such as tetrahydrofuran.

Typically, the reaction is carried out under an inert atmosphere, for example nitrogen, cooled to a temperature of about −78° C. while reacting with the n-butyl lithium and allowed to warm to room temperature after the addition of the DMF.

Compounds of general formula (X) may be prepared by reacting 2-bromothiophenol with a compound of general formula (XI):

R—X     (XI)

Where R is as defined for general formula (I) and X is a leaving group, particularly a halo group such as chloro or bromo.

The reaction may be carried out in the presence of a base, for example caesium carbonate and at a temperature of 20-50° C., typically 40° C.

An alternative route to compounds of general formula (IV) is by reaction of sodium salts of general formula (IX):

R—SO$_2$Na     (IX)

wherein R is as defined for general formula (I) with 2-fluorobenzaldehyde. The reaction may be carried out in a solvent such as dimethylsulfoxide at elevated temperature, typically 80 to 110° C. The reaction may take several days to go to completion.

Sodium salts of general formula (IX) are commercially available.

Compounds of general formula (IV) may also be prepared directly from compounds of general formula (VII) without the need for the protection and deprotection steps. In this procedure a cooled oxidising agent such as meta chloroperoxybenzoic acid may be added to the compound of general formula (VII), typically with cooling to about −5 to 5° C. The reaction mixture may be allowed to warm to 15 to 30° C., usually room temperature, and then reacted with sodium metabisulfite.

As mentioned above, some compounds of general formula (VII) are commercially available.

Compounds of general formula (I) are CRTH2 receptor antagonists and compounds of general formula (II) are prodrugs for compounds of general formula (I). Compounds of general formulae (I) and (II) are therefore useful in a method for the treatment of diseases and conditions mediated by PGD$_2$ or other agonists at the CRTH2 receptor, the method comprising administering to a patient in need of such treatment a suitable amount of a compound of general formula (I) or (II).

In a third aspect of the invention, there is provided a compound of general formula (I) or (II) for use in medicine, particularly for use in the treatment or prevention of diseases and conditions mediated by PGD$_2$ or other CRTH2 receptor agonists.

Furthermore, there is also provided the use of a compound of general formula (I) or (II) in the preparation of an agent for the treatment or prevention of diseases and conditions mediated by CRTH2 receptor agonists, particularly PGD$_2$.

As mentioned above, such diseases and conditions include allergic diseases, asthmatic conditions and inflammatory diseases, examples of which are asthma, including allergic asthma, bronchial asthma, intrinsic, extrinsic, exercise-induced, drug-induced and dust-induced asthma, treatment of cough, including chronic cough associated with inflammatory and secretory conditions of the airways and iatrogenic cough, acute and chronic rhinitis, including rhinitis medicamentosa, vasomotor rhinitis, perennial allergic rhinitis, seasonal allergic rhinitis, nasal polyposis, acute viral infection including common cold, infection due to respiratory syncytial virus, influenza, coronavirus and adenovirus, atopic dermatitis, contact hypersensitivity (including contact dermatitis), eczematous dermatitis, phyto dermatitis, photo dermatitis, sebhorroeic dermatitis, dermatitis herpetiformis, lichen planus, lichen sclerosis et atrophica, pyoderma gangrenosum, skin sarcoid, discoid lupus erythematosus, pemphigus, pemphigoid, epidermolysis bullosa urticaria, angioedema, vasculitides, toxic erythemas, cutaneous eosinophilias, alopecia areata, male-pattern baldness, Sweet's syndrome, Weber-Christian syndrome, erythema multiforme, cellulitis, panniculitis, cutaneous lymphomas, non-melanoma skin cancer and other dysplastic lesions; blepharitis conjunctivitis, especially allergic conjunctivitis, anterior and posterior uveitis, choroiditis, autoimmune, degenerative or inflammatory disorders affecting the retina, ophthalmitis; bronchitis, including infectious and eosinophilic bronchitis, emphysema, bronchiectasis, farmer's lung, hypersensitivity pneumonitis, idiopathic interstitial pneumonias, complications of lung transplantation, vasculitic and thrombotic disorders of the lung vasculature, pulmonary hypertension, food allergies, gingivitis, glossitis, periodontitis, oesophagitis including reflux, eosinophilic gastroenteritis, proctitis, pruris ani, celiac disease, food-related allergies, inflammatory bowel disease, ulcerative colitis and Crohn's disease, mastocytosis and also other CRTH2-mediated diseases, for example autoimmune diseases such as hyper IgE syndrome, Hashimoto's thyroiditis, Graves' disease, Addison's disease, diabetes mellitus, idiopathic thrombocytopaenic purpura, eosinophilic paschiitis, antiphospholipid syndrome and systemic lupus erythematosus, AIDS, leprosy, Sezary syndrome, paraneoplastic syndrome, mixed and undifferentiated connective tissue diseases, inflammatory myopathies including dermatomyositis and polymyositis, polymalgia rheumatica, juvenile arthritis, rheumatic fever, vasculitides including giant cell arteritis, Takayasu's arteritis, Churg-Strauss syndrome, polyarteritis nodosa, microscopic polyarteritis, temporal arteritis, myasthenia gravic, acute and chronic pain, neuropathic pain syndromes, neurodegeneration, central and peripheral nervous system complications of malignant, infectious or autoimmune processes, low back pain, familial Mediterranean Fever, Muckle-Wells syndrome, Familial Hibernian fever, Kikuchi disease, psoriasis, acne, multiple sclerosis, allograft rejection, reperfusion injury, chronic obstructive pulmonary disease, as well as rheumatoid arthritis, Still's disease, ankylosing spondylitis, reactive arthritis, undifferentiated spondarthropathy, psoriatic arthritis, septic arthritis and other infection-related arthopathies and bone disorders and osteoarthritis; acute and chronic crystal-induced synovitis including urate gout, calcium pyrophosphate deposition disease, calcium paptite related tendon syndrome and synovial inflammation, Behcet's disease, primary and secondary Sjogren's syndrome systemic sclerosis and limited scleroderma; hepatitis, cirrhosis of the liver, cholecystitis, pancreatitis, nephritis, nephritic syndrome, cystitis and Hunner's ulcer, acute and chronic urethritis, prostatitis, epididymitis, oophoritis, salpingitis, vulvo-vaginitis, Peyronie's disease, erectile dysfunction, Alzheimer's disease and other dementing disorders; pericarditis, myocarditis, inflammatory and auto-immune cardiomyopathies including myocardial sarcoid, ischaemic reperfusion injuries, endocarditis, valvulitis, aortitis, phlebitis, thrombosis, treatment of common cancers and fibrotic conditions such as idiopathic pulmonary fibrosis including cryptogenic fibrosing alveolitis, keloids, excessive fibrotic scarring/adhesions post surgery, liver fibrosis including that associated with hepatitis B and C, uterine fibroids, sarcoidosis, including neurosarcoidosis, scleroderma, kidney fibrosis resulting from diabetes, fibrosis associated with RA, atherosclerosis, including cerebral atherosclerosis, vasculitis, myocardial fibrosis resulting from myocardial infarction, cystic fibrosis, restenosis, systemic sclerosis, Dupuytren's disease, fibrosis complicating anti-neoplastic therapy and chronic infection including tuberculosis and aspergillosis and other fungal infections, and CNS fibrosis following stroke. The compounds are also of use in the promotion of healing without fibrotic scarring.

The compounds of general formula (I) or (II) must be formulated in an appropriate manner depending upon the diseases or conditions they are required to treat.

Therefore, in a further aspect of the invention there is provided a pharmaceutical composition comprising a compound of general formula (I) or (II) together with a pharmaceutical excipient or carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) or (II) in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) or (II) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) or (II) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the compound will be about 0.01 to 100 mg/kg; so as to maintain the concentration of drug in the plasma at a concentration effective to inhibit $PGD_2$ at the CRTH2 receptor. The precise amount of a compound of general formula (I) or (II) which is therapeutically effective, and the route by which such compound is best administered, is readily determined by one of ordinary skill in the art by comparing the blood level of the agent to the concentration required to have a therapeutic effect.

Compounds of general formula (I) or (II) may be used in combination with one or more active agents which are useful in the treatment of the diseases and conditions listed above, although these active agents are not necessarily inhibitors of $PGD_2$ at the CRTH2 receptor.

Therefore, the pharmaceutical composition described above may additionally contain one or more of these active agents.

There is also provided the use of a compound of general formula (I) or (II) in the preparation of an agent for the treatment of diseases and conditions mediated by CRTH2 receptor agonists, especially $PGD_2$, wherein the agent also comprises an additional active agent useful for the treatment of the same diseases and conditions.

These additional active agents may be other CRTH2 receptor antagonists or may have a completely different mode of action. They include existing therapies for allergic and other inflammatory diseases including:

Suplatast tosylate and similar compounds;

$\beta_1$ to $\beta_4$ adrenoreceptor agonists such as metaproterenol, isoproterenol, isoprenaline, albuterol, salbutamol, formoterol, salmeterol, terbutaline, orciprenaline, bitolterol mesylate and pirbuterol or methylxanthanines such as theophylline and aminophylline, mast cell stabilisers such as sodium cromoglycate or muscarinic receptor (M1, M2 or M4) antagonists;

antihistamines, for example histamine $H_1$ receptor antagonists such as loratidine cetirizine, desloratidine, fexofenadine, astemizole, azelastine and chlorpheniramine or histamine $H_2$ or $H_4$ receptor antagonists;

$\alpha_1$ and $\alpha_2$ adrenoreceptor agonists such as propylhexedrine phenylephrine, phenylpropanolamine, pseudoephedrine, naphazoline hydrochloride, oxymetazoline hydrochloride, tetrahydrozoline hydrochloride, xylometazoline hydrochloride and ethylnorepinephrine hydrochloride;

insulin-like growth factor (IGF-1) mimetics;

matrix metalloprotease (MMP) inhibitors, for example inhibitors of stromelysins, collagenases gelatinases and aggrecanase, especially collagenase-1, collagenase-2, collagenase-3, stromelysin-1, stromelysin-2, stromelysin-3 and MMP-12;

modulators of chemokine receptor function, for example CCR1, CCR2, CCR2A, CCR2B, CCR3, CCR4, CCR5, CCR6, CCR7, CCR8, CCR9, CCR10 and CCR11 (for the C—C family) or CXCR1, CXCR2, CXCR3, CXCR4 and CXCR5 (for the C—X—C family) and $CX_3CR1$ for the C—$X_3$—C family;

antiviral agents such as Viracept, AZT, acyclovir and famiciclovir and antisepsis compounds such as Valant;

cardiovascular agents, for example calcium channel blockers, lipid lowering agents such as statins, fibrates, beta-blockers, ACE inhibitors, Angiotensin-2 receptor antagonists and platelet aggregation inhibitors;

CNS agents, for example antidepressants such as sertraline, anti-Parkinsonian drugs such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, nicotine antagonists, Dopamine agonists and inhibitors of neuronal nitric oxide synthase and anti-Alzheimer's drugs such as donepezil, tacrine, COX-2 inhibitors, propentofylline or metryfonate;

Tryptase inhibitors;

Platelet activating factor (PAF) antagonists;

Interleukin converting enzyme (ICE) inhibitors;

IMPDH inhibitors;

Adhesion molecule inhibitors including VLA-4 antagonists;

Cathepsins;

MAP kinase inhibitors;

Glucose-6-phosphonate dehydrogenase inhibitors;

Kinin-$B_1$ and $B_2$ receptor antagonists;

Anti-gout agents such as colchicine;

Xanthine oxidase inhibitors such as allopurinol;

Uricosuric agents, such as probenecid, dulfinpyrazone and benzbromarone;

Growth hormone secretagogues;

Transforming growth factor beta (TGFβ);

Platelet-derived growth factor (PGDF)

Fibroblast growth factor e.g. basic fibroblast growth factor

Granulocyte macrophage colony stimulating factor (GM-CSF);

Capsaicin;

Tachykinin $NK_1$ and $NK_3$ receptor antagonists such as NKP-608C, talnetant and D-4418;

Elastase inhibitors such as UT-77 and ZD-0892;

Induced nitric oxide synthase inhibitors (iNOS);

Osteoporosis agents such as roloxifene, droloxifene, lasofoxifene or fosomax;

anticholinergic agents such as ipratropium bromide, tiotropium bromide, oxitropium bromide, pirenzepine and telenzepine;

leukotriene antagonists (LTB$_4$, LTD$_4$ and LTE$_4$ antagonists) such as phenothiazine-3-ones such as L-651,392, amidino compounds such as CGS-25019c, benzoxalamines such as ontazolast, benzene carboximidamides such as BIIL 284/260 and compounds such as zafirlukast, ablukast, montelukast, pranlukast, verlukast, RG-12525, Ro-245913, iralukast and BAY x 7195;

leukotriene biosynthesis inhibitors such as 5-lipoxygenase inhibitors or 5-lipoxygenase activating protein (FLAP) inhibitors such as zileuton, ABT-761, fenleuton, tepoxalin, Abbott-79175, N-(5-substituted)-thiophene-2-alkylsolfonamides, 2,6-di-tert-butylphenol hydrazones, methoxytetrahydropyrans such as ZD2138, SB-210661, pyridinyl-substituted-2-cyanonaphthalene compounds such as L-739010, 2-cyanoquinoline compounds such as L-746,530, indole and quinoline compounds such as MK-591, MK-886 and BAY x 1005;

Phosphodiesterase inhibitors, including PDE4 inhibitors such as PDE4D inhibitors;

anti-IgE antibody therapies such as omalizumab;

anti-infectives such as fusidic acid (particularly for the treatment of atopic dermatitis);

anti-fungals such as clotrimazole (particularly for the treatment of atopic dermatitis);

immunosuppressants such as tacrolimus and particularly pimecrolimus in the case of inflammatory skin disease or alternatively FK-506, rapamycin, cyclosporine, azathioprine or methotrexate;

antiproliferative/antineoplastic drugs such as alkylating agents, e.g. cisplatin, carboplatin, cyclophosphamide, nitrogen mustard, melphalan, chlorambucil, busulphan and nitrosoureas, antimetabolites, e.g. antifolates such as fluoropyrimidines such as 5-fluorouracil and tegafur, raltitrexed, methotrexate, cytosine arabinoside, hydroxyurea, gemcitabine and paclitaxel;

antitumour antibiotics such as anthracyclines such as adriamycin, bleomycin, doxorubicin, daunomycin, epirubicin, idarubicin, mitomycin-C, dactinomycin and methramicin; antimitotic agents such as vinca alkaloids including vincristine, vinblastine, vindesine and vinorelbine and taxoides such as taxol and taxostere and topoisomerase inhibitors such as epipodophyllotoxins like etoposide and teniposide, amsacrine, topotecan and camptothecin; cytostatic agents such as antioestrogens such as tamoxifen, toremifene, raloxifene, droloxifene and iodoxyfene, oestrogen receptor down regulators such as fulvestrant, antiandrogens such as bicalutamide, flutamide, nilutamide and cyproterone acetate, LHRH antagonists or agonists such as goserelin, leuprorelin and buserelin, progestogens such as megestrol acetate, aromatase inhibitors such as anastrozle, letrozole, borazole and exemestane and inhibitors of 5α reductase such as finasteride;

agents which inhibit cancer cell invasion, for example metalloproteinase inhibitors such as marimastat and inhibitors of urokinase plasminogen activator receptor function;

inhibitors of growth factor function for example growth factor antibodies, growth factor receptor antibodies, e.g. the anti-erbb2 antibody trastuzumab and the anti-erbb1 antibody cetuximab, farnesyl transferase inhibitors, tyrosine kinase inhibitors and serine or threonine kinase inhibitors, for example inhibitors of the epidermal growth factor family such as EGFR family tyrosine kinase inhibitors such as N-(3-chloro-4-fluorophenyl)-7-methoxy-6-(3-morphoinopropoxy)quinazolin-4-amine (gefitinib), N-(3-ethynylphenyl)-6,7-bis(2-methoxyethoxy)quinazolin-4-amine (erlotinib) and 6-acrylamido-N-(3-chloro-4-fluorophenyl)-7-(3-morpholinopropoxy)quinazolin-4-amine (CI 1033), or inhibitors of the platelet derived growth factor or the hepatocyte growth factor families;

antiangiogenic agents, particularly those which inhibit the effects of vascular endothelial growth factor e.g. the anti-vascular endothelial cell growth factor antibody bevacizumab and also compounds that work by other mechanisms e.g. linomide, inhibitors of integrin αvβ3 funciton and angiostatin;

vascular damaging agents such as Combretastatin A4;

antisense therapies such as those which are directed to targets listed above, e.g. ISIS 2503, an anti-ras antisense;

gene therapy agents, including agents for replacing aberrant genes such as aberrant p53, or aberrant BRCA1 or BRCA2, GDEPT (gene-directed enzyme pro-drug therapy), cytosine deaminase, thymidine kinase or a bacterial nitroreductase enzyme or agents for increasing patient tolerance to chemotherapy or radiotherapy such as multi-drug resistant gene therapy;

immunotherapy agents including in vivo and ex vivo approaches to increase the immunogenicity of patient tumour cells such as transfection with cytokines such as IL2, IL4 or GMCSF, approaches to decrease T-cell anergy, approaches using transfected immune cells such as cytokine-transfected dentritic cells or approaches using cytokine-transfected tumour cell lines or anti-idiotypic antiobodies;

corticosteroids such as prednisone, prednisolone, flunisolide, triamcinolone acetonide, beclomethasone dipropionate, budesonide, fluticasone propionate and mometasone furoate and hyaluronic acids such as hyalgan and synvisc and P2X7 receptor antagonists;

drugs which promote Th1 cytokine response such as interferons, TNF or GM-CSF.

CRTH2 antagonists may also be combined with:

other antagonists of PGD$_2$ acting at other receptors such as DP antagonists;

inhibitors of phosphodiesterase type 4 such as cilonilast;

drugs that modulate cytokine production such as inhibitors of TNFα converting enzyme (TACE) anti-TNF monoclonal antibodies, TNF receptor immunoglobulin molecules, inhibitors of other TNF isoforms, non-selective COX-1/COX-2 inhibitors such as piroxicam, diclofenac, propionic acids such as naproxen, flubiprofen, fenoprofen, ketoprofen and ibuprofen, fenamates such as mefanamic acid, indomethacin, sulindac and apazone, pyrazolones such as phenylbutazone, salicilates such as aspirin; COX-2 inhibitors such as meloxicam, celecoxib, fofecoxib, valdecoxib and etoricoxib, low dose methotrexate, lefunomide, ciclesonide, hydroxychloroquine, d-penicillamine, auranofin or parenteral or oral gold.

drugs that modulate the activity of Th2 cytokines IL-4 and IL-5 such as blocking monoclonal antibodies and soluble receptors;

PPAR-γ agonists such as rosiglitazone; or with anti-RSV antibodies such as Synagis (palivizumab) and agents that may be used to treat rhinovirus infection in the future e.g. interferon-beta and other interferons In yet a further aspect of the invention, there is provided a product comprising a compound of general formula (I) or (II) and one or more of the agents listed above as a combined preparation for simultaneous, separate or sequential use in the treatment of a disease or condition mediated by the action of PGD$_2$ at the CRTH2 receptor.

The invention will now be described in greater detail with reference to the following non limiting examples and the drawings in which.

PREPARATION OF COMPOUNDS OF GENERAL FORMULA I

Figure 1:
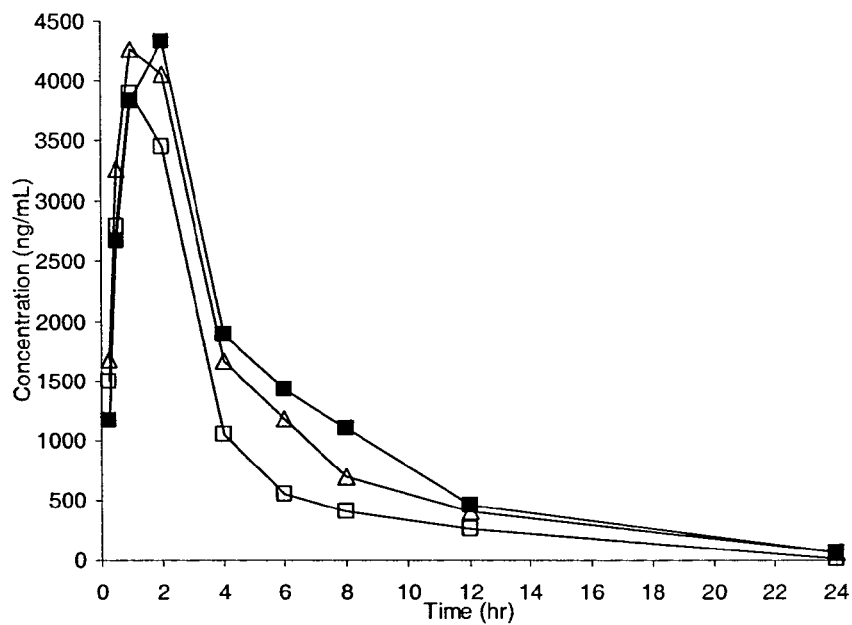
FIG. 1 is a plot of blood concentration of Compound 1 versus time for rats dosed orally with 3 mg/kg of Compound 1.

The compounds of Examples 1 to 3 were prepared according to the following reaction schemes.

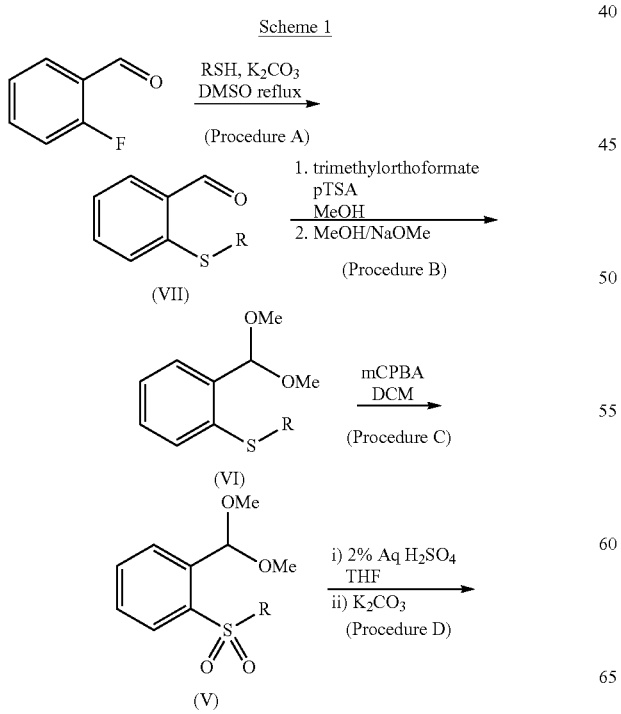

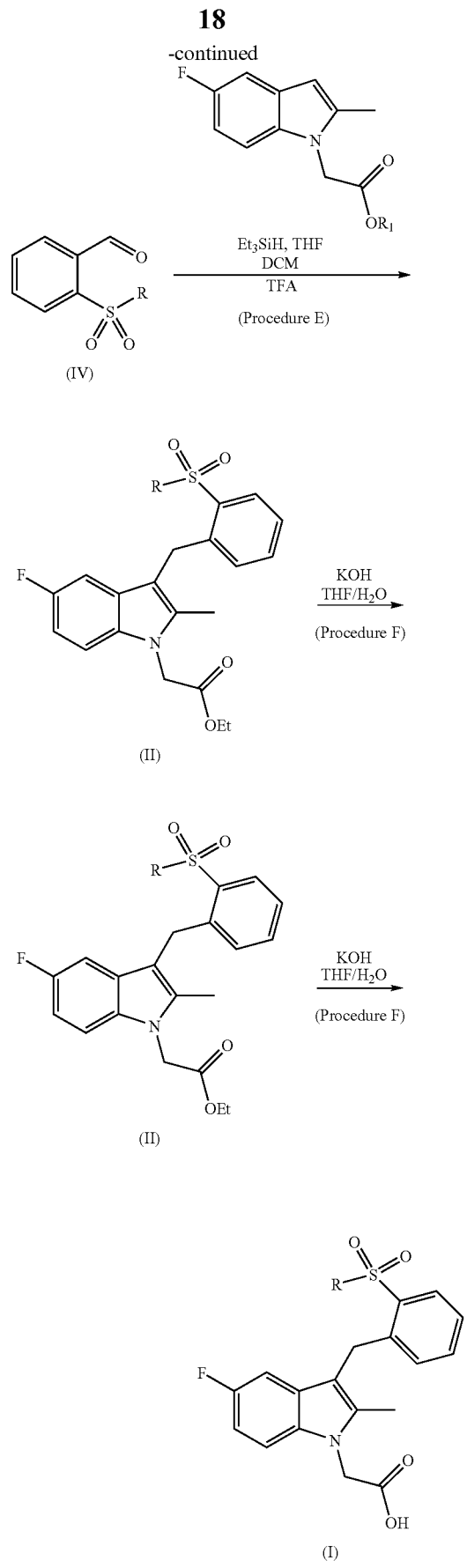

Scheme 2

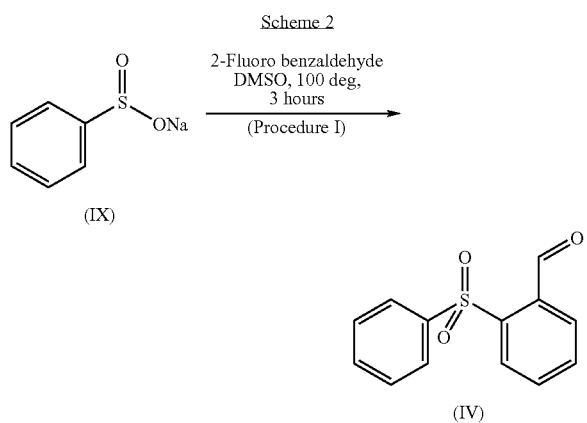

Scheme 3

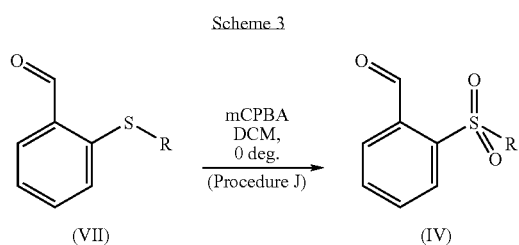

Example 1

Preparation of 2-(5-fluoro-2-methyl-3-(2-(phenylsulfonyl)benzyl)-1H-indol-1-yl)acetic acid (Compound 1)

From commercial benzenesulfinic acid sodium salt and 2-fluorobenzaldehyde.

a) Procedure I. ($S_NAr$) to Yield 2-(phenylsulfonyl)benzaldehyde

To a solution of 2-fluoro benzaldehyde (5.00 ml, 47.6 mmol) in dimethyl sulfoxide (45 ml) was added benzene sulfinic acid sodium salt (8.60 g, 52.4 mmol) and the resulting mixture heated to 100° C. Upon heating the sulfinic acid salt dissolved. The solution was heated at 100° C. for 3 days. The reaction was cooled to room temperature and water (50 ml) added. This mixture was extracted with ethyl acetate, the combined organic extracts were washed with saturated brine, dried over $MgSO_4$ and concentrated in vacuo. The crude material was purified by flash chromatography on silica eluting with 25% ethyl acetate:petroleum ether (40-60° C.) to 33% ethyl acetate:petroleum ether (40-60° C.) to give (4.12 g, 16.7 mmol, 35%). $\delta_H$ (300 MHz, $d_6$-DMSO) 10.68 (1H, s, CHO), 8.26-8.17 (1H, m, Ar), 8.08-7.99 (2H; m, Ar), 7.99-7.89 (3H, m, Ar) and 7.80-7.62 (3H, m, Ar).

b) Procedure E. (Reductive alkylation) to Yield ethyl 2-(5-fluoro-2-methyl-3-(2-(phenylsulfonyl)benzyl)-1H-indol-1-yl)acetate To a solution of 2(5-fluoro-2-methyl-1H-indol-1-yl)acetic acid ethyl ester (1.29 g, 1.49 mmol), 2-(phenylsulfonyl)benzaldchyde (1.50 g, 6.10 mmol) and triethylsilane (4.30 ml, 27.0 mmol) in dichloromethane (40 ml) was added trifluoroacetic acid (1.25 ml, 16.5 mmol) dropwise under $N_2$ at 0° C. over 30 minutes. The reaction was warmed to room temperature and stirred for 2 hours. Saturated aqueous sodium hydrogen carbonate solution was added and the product extracted with dichloromethane. The combined organic extracts were washed with saturated brine, dried over $MgSO_4$ and concentrated in vacuo giving a brown oil which was triturated with petroleum ether (40-60° C.) to give a white solid (1.34 g, 2.88 mmol 52%). $\delta_H$ (300 MHz, $CDCl_3$) 8.36-8.30 (1H, m, Ar), 8.00-7.93 (2H, m, Ar), 7.68-7.52 (3H, Ar), 7.45-7.33 (2H, m, Ar), 7.05 (1H, dd, J 8.6 and 4.3 Hz, Ar), 6.06-6.90 (1H, m, Ar), 6.82 (1H, td, J 9.1 and 2.7 Hz, Ar), 6.24 (1H, dd, J 9.5 and 2.4 Hz, Ar), 4.76 (2H, s, $NCH_2$), 4.22 (2H, s, $ArCH_2Ar$), 4.21 (2H, q, J 7.1 Hz, $CH_2CH_3$), 2.14 (3H, s, $CH_3$) and 1.27 (3H, t, J 7.1 Hz, $CH_2CH_3$).

c) Procedure F (Saponification) to Yield 2-(5-fluoro-2-methyl-3-(2-(phenylsulfonyl)benzyl)-1H-indol-1-yl)acetic acid To a stirred solution of ester product of step (b) (1.33 g, 2.86 mmol) in tetrahydrofuran (15 ml) was added a solution of aqueous KOH (500 mg, 8.57 mmol) in water (15 ml). After 2 hours the tetrahydrofuran was removed under reduced pressure and the basic aqueous layer was washed with ethyl acetate. The remaining aqueous layer was acidified with HCl (2N) and extracted with ethyl acetate. The combined organic extracts were washed with saturated brine, dried over $MgSO_4$ and concentrated in vacuo giving a brown solid which was triturated with a mixture of diethyl ether and petroleum ether (40-60° C.) to give white solid (1.14 g, 2.61 mmol 91%).

$\delta_H$ (300 MHz, $d_6$-DMSO) 13.00 (1H, bs, $CO_2H$), 8.26-8.20 (1H, m, Ar), 7.99-7.93 (2H, m, Ar), 7.80-7.62 (3H, m, Ar), 7.55-7.48 (2H, m, Ar), 7.34 (1H, dd, J 8.6 and 4.3 Hz, Ar), 6.93-6.87 (1H, m, Ar), 6.81 (1H, td, J 9.1 and 2.7 Hz, Ar), 6.18 (1H, dd, J 9.7 and 2.4 Hz, Ar), 4.95 (2H, s, $NCH_2$), 4.14 (2H, s, $ArCH_2Ar$) and 2.06 (3H, s, $CH_3$). Tr=4.62 min (95%), m/z (M+H)$^+$ 438.3.

Example 2

Preparation of 2-(3-(2-(4-chlorophenylsulfonyl)benzyl)-5-fluoro-2-methyl-1H-indol-1-yl)acetic acid (Compound 2)

From commercial 2-(4-chlorophenylthio)benzaldehyde.

a) Procedure J. (Direct Oxidation) to Yield 2-(4-chlorophenylsulfonyl)benzaldehyde To a solution of 2-(4-chlorophenylthio)benzaldehyde (2.00 g, 8.00 mmol) in dichloromethane (20 mL) at 0° C. was added meta chloroperoxybenzoic acid (77% max, 5.40 g, 24.17 mmol) in portions over 15 minutes, then warmed to room temperature and stirred for 2 hours. Aqueous sodium metabisulfite solution was added carefully until effervescence ceased. This solution was extracted with dichloromethane and the combined organic extracts were washed with NaOH (1N) then saturated brine, dried over $MgSO_4$ and concentrated in vacuo giving a white solid (1.05 g, 3.74 mmol, 46%). $\delta_H$ (300 MHz, $d_6$-DMSO) 10.69 (1H, s, CHO), 8.25-8.18 (1H, m, Ar), 8.07-8.00 (2H, m, Ar), 8.00-7.90 (3H, m, Ar) and 7.81-7.64 (3H, m, Ar).

b) Procedure E. (Reductive Alkylation) to Yield ethyl 2-(3-(2-(4-chlorophenylsulfonyl)benzyl)-5-fluoro-2-methyl-1H-indol-1-yl)acetate $\delta_H$ (300 MHz, $CDCl_3$) 8.33-8.26 (1H, m, Ar), 7.89-7.82 (2H, m, Ar), 7.53-7.46 (2H, m, Ar), 7.44-7.73 (2H, m, Ar), 7.06 (1H, dd, J 8.6 and 4.3 Hz, Ar), 7.02-6.96 (1H, m, Ar), 6.84 (1H, td, J 9.1 and 2.7 Hz, Ar), 6.33 (1H, dd, J 9.5 and 2.4 Hz, Ar), 4.76 (2H, s, $NCH_2$), 4.23 (2H, s, $ArCH_2Ar$), 4.22 (2H, q, J 7.2 Hz, $CH_2CH_3$), 2.16 (3H, s, $CH_3$) and 1.27 (3H, t, J 7.2 Hz, $CH_2CH_3$).

c) Procedure F. (Saponification) to Yield 2-(3-(2-(4-chlorophenylsulfonyl)benzyl)-5-fluoro-2-methyl-1H-indol-1-yl)acetic acid $\delta_H$ (300 MHz, $d_6$-DMSO) 13.01 (1H, bs, $CO_2H$), 8.27-8.20 (1H, m, Ar), 7.97-7.90 (2H, m, Ar), 7.74-7.67 (2H, m, Ar), 7.57-7.51 (2H, m, Ar), 7.34 (1H, dd, J 8.7 and 4.3 Hz, Ar), 7.00-6.93 (1H, m, Ar), 6.81 (1H, td, J 9.4 and 2.6 Hz, Ar), 6.16 (1H, dd, J 9.8 and 2.6 Hz, Ar), 4.95 (2H, s, $NCH_2$), 4.17 (2H, s, $ArCH_2Ar$) and 2.12 (3H, s, $CH_3$). Tr=4.04 min (96%), m/z $(M+H)^+$ 472.0.

Example 3

Preparation of 2-(5-fluoro-3-(2-(4-fluorophenylsulfonyl)benzyl)-2-methyl-1H-indol-1-yl)acetic acid (Compound 3)

a) Procedure A. ($S_NAr$) to Yield 2-(4-fluorophenylthio)benzaldehyde

To a suspension of 4-fluorophenylthiol (0.86 ml, 8.06 mmol) and $K_2CO_3$ (2.50 g, 18.12 mmol) in DMSO (5 ml) was added 2-fluorobenzaldehyde (1.00 g, 8.06 mmol) under $N_2$ and the mixture heated at 100° C. for 3 hours. The reaction was cooled to room temperature and water (20 ml) added. This mixture was extracted with ethyl acetate, the combined organic extracts were washed with saturated brine, dried over $MgSO_4$ and concentrated in vacuo to give a yellow solid (1.20 g, 5.17 mmol, 64%) $\delta_H$ (300 MHz, $d_6$-DMSO) 10.23 (1H, s, CHO), 7.98 (1H, dd, J 7.3 and 1.7 Hz, Ar), 7.63-7.49 (3H, m, Ar), 7.45-7.32 (3H, m, Ar) and 6.88 (1H, d, J 7.7 Hz, Ar).

b) Procedure B. (Aldehyde Protection) to Yield (2-(dimethoxymethyl)phenyl)(4-fluorophenyl)sulfane To a solution of the aldehyde product of step (a) (1.20 g, 5.17 mmol) and trimethylorthoformate (0.62 ml, 0.58 mmol) in anhydrous methanol (80 ml) was added p-toluenesulfonic acid (0.10 g, 0.58 mmol) under $N_2$ and the mixture stirred at room temperature for 72 hours. A solution of sodium methoxide in methanol (0.12 ml, 25% sol, 0.58 mmol) was added and all solvent removed in vacuo giving a colourless oil (1.50 g). No further purification was carried out.

$\delta_H$ (300 MHz, $CDCl_3$) 7.64 (1H, dd, J 7.3 and 2.0 Hz, Ar), 7.38-7.30 (2H, m, Ar), 7.29-7.19 (2H, m, Ar), 7.15-7.10 (1H, m, Ar), 7.07-6.99 (2H, m, Ar), 5.72 (1H, s, $CH(CH_3)_2$) and 3.37 (6H, s, $CH(CH_3)_2$).

c) Procedure C. (Oxidation) to Yield 1-(dimethoxymethyl)-2-(4-fluorophenylsulfonyl)benzene To a solution of the sulfide product of step (b) (1.50 g) in dichloromethane (40 ml) was added 3-chloroperoxybenzoic acid (4.60 g, 20.59 mmol) portionwise over 30 minutes at 0° C. The reaction was warmed to room temperature and stirred for 2 hours. Aqueous sodium metabisulfite solution (50 ml) was added and the product extracted with dichloromethane. The combined organic extracts were washed with NaOH (50 ml, 1N) followed by saturated brine, dried over $MgSO_4$ and concentrated in vacuo to give a yellow oil (1.40 g, 4.52 mmol 87% over 2 steps).

$\delta_H$ (300 MHz, $CDCl_3$) 8.11 (1H, dd, J 8.1 and 1.5 Hz, Ar), 7.85 (2H, dd, J 8.9 and 5.0 Hz Ar), 7.76 (1H, dd, J 7.9 and 1.5 Hz, Ar), 7.58 (1H, ddd J 7.8, 7.6 and 1.4 Hz, Ar), 7.47 (1H, ddd J 7.8, 7.6 and 1.4 Hz, Ar), 7.14-7.05 (2H, m, Ar), 6.12 (1H, s, $CH(CH_3)_2$) and 3.12 (6H, s, $CH(CH_3)_2$).

d) Procedure D. (Acetal Deprotection) to Yield 2-(4-fluorophenylsulfonyl)benzaldehyde To a solution of 1-(dimethoxymethyl)-2-(4-fluorophenylsulfonyl)benzene (1.40 g, 4.52 mmol) in tetrahydrofuran (20 ml) was added aqueous sulphuric acid (20 ml, 2% solution) and stirred at room temperature for 12 hours. Solid $K_2CO_3$ was added until effervescence ceased and the solution was basic. The solution was extracted with ethyl acetate, the combined organic extracts were washed with saturated brine, dried over $MgSO_4$ and concentrated in vacuo to give a yellow solid (0.90 g, 340 mmol 75%).

$\delta_H$ (300 MHz, $CDCl_3$) 10.85 (1H, s, CHO), 8.21-8.16 (1H, m, Ar), 8.08-8.02 (1H, m, Ar), 7.97-7.90 (2H, m, Ar), 7.80-7.74 (2H, m, Ar) and 7.27-7.19 (2H, m, Ar).

e) Procedure E. (Reductive Alkylation) to Yield ethyl 2-(5-fluoro-3-(2-(4-fluorophenylsulfonyl)benzyl)-2-methyl-1H-indol-1-yl)acetate $\delta_H$ (300 MHz, $CDCl_3$) 8.32-8.26 (1H, m, Ar), 8.00-7.90 (2H, m, Ar), 7.43-7.37 (2H, m, Ar), 7.26-7.17 (2H, m, Ar), 7.06 (1H, dd, J 8.8 and 4.3 Hz, Ar), 7.00-6.94 (1H, m, Ar), 6.84 (1H, td, J 9.1 and 2.6 Hz, Ar), 6.32 (1H, dd, J 9.5 and 2.6 Hz, Ar), 4.77 (2H, s, $NCH_2$), 4.24 (2H, s, $ArCH_2Ar$), 4.22 (2H, q, J 7.2 Hz, $CH_2CH_3$), 2.16 (3H, s, $CH_3$) and 1.27 (3H, t, J 7.2 Hz, $CH_2CH_3$).

f) Procedure F. (Saponification) to Yield 2-(5-fluoro-3-(2-(4-fluorophenylsulfonyl)benzyl)-2-methyl-1H-indol-1-yl)acetic acid $\delta_H$ (300 MHz, $d_6$-DMSO) 13.00 (1H, bs, $CO_2H$), 8.27-8.20 (1H, m, Ar), 8.08-8.00 (2H, m, Ar), 7.60-7.45 (4H, m, Ar), 7.35 (1H, dd, J 8.7 and 4.3 Hz, Ar), 6.99-6.93 (1H, m, Ar), 6.83 (1H, td, J 9.0 and 2.3 Hz, Ar), 6.17 (1H, dd, J 9.8 and 2.6 Hz, Ar), 4.98 (2H, s, $NCH_2$), 4.18 (2H, s, $ArCH_2Ar$) and 2.13 (3H, s, $CH_3$). Tr=4.60 min (95%), m/z $(M+H)^+$ 456.3

Example 4

Human Whole Blood Eosinophil Shape Change Assay

Compounds 1 to 3 were assayed for their effect on PGD2 induced eosinophil shape change and were compared with Comparator Compounds A to G.

Comparator Compound A is (5-Fluoro-2-methyl-3-quinolin-2-ylmethyl-indol-1-yl)-acetic acid.

Comparator Compound B is [5-Fluoro-3-(4-methanesulfonyl-benzyl)-2-methyl-indol-1-yl]-acetic acid.

Comparator Compound C is 2-{5-Fluoro-2-methyl-3-[4-(phenylsulfonyl)benzyl]-1H-indol-1-yl}acetic acid (the 4-regioisomer of Compound 1).

Comparator Compound D is 2-{3-[4-(4-chlorophenylsulfonyl)benzyl]-5-fluoro-2-methyl-1H-indol-1-yl}acetic acid (the 4-regioisomer of Compound 2).

Comparator Compound E is 2-{5-Fluoro-3-[4-(4-fluorophenylsulfonyl)benzyl]-2-methyl-1H-indol-1-yl}acetic acid (the 4-regioisomer of Compound 3).

Comparator Compound F is 2-{5-Fluoro-2-methyl-3-[3-(phenylsulfonyl)benzyl]-1H-indol-1-yl}acetic acid (the 3-regioisomer of Compound 1).

Comparator Compound G is 2-{3-[3-(4-chlorophenylsulfonyl)benzyl]-5-fluoro-2-methyl-1H-indol-1-yl}acetic acid (the 3-regioisomer of Compound 2).

Methods

Shape Change Assay in Whole Blood

Compounds (1 µl, 200× final concentration) were added directly to 200 µl whole blood, mixed well and incubated for 15 min, 37° C., 5% $CO_2$. After this time, cell shape was fixed by addition of 300 µl Cytofix™ buffer (BD Biosciences), 15 min on ice. 10 ml RBC lysis buffer was added to the fixed cells, incubated 5 min, at room temperature and centrifuged, 300×g for 5 min. Supernatant (containing lysed red cells) was removed and the lysis step was repeated. Leukocytes were resuspended in 250 µl RPMI/10% FCS and shape change analysed by FACS. Eosinophils were gated out based on their autofluorescence and 2000 eosinophil events were counted per sample. Data were analysed in triplicate.

Results

The results for the eosinophil shape change assay are shown in Table 1.

All the compounds bound CRTH2 with a Ki of less than 0.012 μM. It can be seen from Table 1 that Compounds 1 to 3 all have excellent $IC_{50}$ values in this assay. Comparator Compound B has comparable activity in this assay to Compounds 1 to 3 but the activity of Compound A is much lower. However, Comparator Compounds C to G, which are the para- and meta-regioisomers of Compounds 1 to 3 have comparatively poor activity in this test (of the order of 10 to 1000 times lower than that of Compounds 1 to 3).

TABLE 1

$IC_{50}$ Values for the Effect of Test Compounds on 10 nm PGD2-induced Eosinophil Shape Change

| Compound | Whole Blood $IC_{50}$ (μM) | | |
|---|---|---|---|
| | Value | SEM | n |
| 1 | 0.005 | 0.003 | 3 |
| 2 | 0.002 | 0.001 | 3 |
| 3 | 0.006 | 0.003 | 3 |
| A | 0.103 | 0.009 | 4 |
| B | 0.008 | 0.002 | 3 |
| C | 0.273 | 0.175 | 3 |
| D | 0.494 | NA | 1 |
| E | 0.071 | 0.008 | 2 |
| F | 1.50 | N/A | 1 |
| G | 4.66 | N/A | 1 |

Example 5

Investigation of Pharmacokinetics of Compounds of General Formula (I) Following Oral Administration in the Rat Experimental Procedures a) Weighing of Rats Rats were weighed on the day of dosing.

b) Dose Preparation

The test material was prepared as a 0.3 mg/mL suspension in 1% carboxy-methyl-cellulose (CMC).

c) Dose Regimen

Three groups of 3 rats were dosed as follows:

| Group No. | Treatment | Dose (mg/kg) | Route |
|---|---|---|---|
| 1 | Compound 1 | 3 | oral |
| 2 | Compound 2 | 3 | oral |
| 3 | Compound 3 | 3 | oral | d) Dose Administration

Doses were administered as a single oral dose using a gavage tube at a constant dose volume of 10 mL/kg.

e) Blood Sample Collection

At each sampling time point blood samples (approximately 0.3 mL) was taken from a catheter inserted into a lateral tail vein prior to the start of the experiment. The final blood sample (approximately 2 mL) from each animal was taken by cardiac puncture under isoflurane anaesthesia following which the animal was killed by exsanguination. Blood samples were taken into individual heparinised containers. Blood samples were collected at the following times post-dose: 15, 30, 60, 120, 240, 360, 480, 720 minutes and 24 hours Following collection, the blood samples were centrifuged (approximately 10,000×g, 2 min at 4° C.) and the plasma stored as one aliquot at approximately −20° C. pending analysis of drug concentrations by LC-MS/MS.

f) Sample Bioanalysis

The plasma samples were analysed for test material concentrations at BioDynamics using an LC-MS/MS method developed at BioDynamics.

Results

The pharmacokinetic profile of a compound is important as it illustrates how much of a compound will remain in the body for how long and the exposure of a subject to a compound when administered orally.

The results for the blood concentrations of Compounds 1, 2, 3, A and B are shown in Tables 2, 3, 4, 5 and 6 respectively.

A compound which is intended to be administered orally, will ideally need to be taken only once or twice daily as this reduces the burden on the patient and thus increases patient compliance. Therefore, it is greatly preferred that after 12 hours, the concentration of drug remaining in the blood is as at least as great as the $IC_{50}$ value for the compound and preferably considerably higher than this. An even more favourable pharmacokinetic profile is one in which the concentration remaining in the blood after 24 hours is at least as great as the $IC_{50}$ value for the compound and preferably considerably higher than this.

TABLE 2

Concentration of Compound 1 in blood (ng/mL) after oral administration to rats at a dose of 3 mg/kg

| Time | Concentration in Blood (ng/mL) | | | | |
|---|---|---|---|---|---|
| (h) | Male 4 | Male 5 | Male 6 | Mean | SD |
| 0.25 | 1161.2 | 1496.0 | 1678.0 | 1445.1 | 262.1 |
| 0.5 | 2681.3 | 2792.4 | 3264.7 | 2912.8 | 309.8 |
| 1 | 3835.5 | 3895.3 | 4262.9 | 3997.9 | 231.4 |
| 2 | 4330.9 | 3454.7 | 4051.1 | 3945.6 | 447.5 |
| 4 | 1890.9 | 1046.5 | 1670.8 | 1536.1 | 438.0 |
| 6 | 1423.7 | 547.5 | 1183.1 | 1051.4 | 452.7 |
| 8 | 1099.9 | 404.7 | 696.2 | 733.6 | 349.1 |
| 12 | 455.4 | 256.6 | 412.8 | 374.9 | 104.7 |
| 24 | 68.5 | 10.2 | 63.5 | 47.4 | 32.3 |

The results in Table 2 show that after 24 hours, the mean amount of Compound 1 remaining in the blood was 47.4 ng/mL. The $IC_{50}$ of Compound 1 in the whole blood eosinophil shape change assay is 5 nM (2.2 ng/ml) and is therefore ca. 21 times over the whole blood eosinophil shape change $IC_{50}$ at 24 hrs. The results therefore show that Compound 1 is particularly suitable for oral administration to a patient.

TABLE 3

Concentration of Compound 2 in blood (ng/mL) after oral administration to rats at a dose of 3 mg/kg

| Time (h) | Male 7 | Male 8 | Male 9 | Mean | SD |
|---|---|---|---|---|---|
| 0.25 | 1569.4 | 1297.7 | 1608.1 | 1491.7 | 169.1 |
| 0.5 | 2612.1 | 1770.2 | 2276.6 | 2219.6 | 423.8 |
| 1 | 2958.2 | 2367.1 | 3366.1 | 2897.1 | 502.3 |
| 2 | 2239.9 | 2536.9 | 2717.6 | 2498.1 | 241.2 |
| 4 | 1128.4 | 1319.1 | 1666.5 | 1371.3 | 272.8 |
| 6 | 519.6 | 368.3 | 1032.6 | 640.2 | 348.2 |
| 8 | 423.7 | 186.7 | 740.4 | 450.3 | 277.8 |

TABLE 3-continued

Concentration of Compound 2 in blood (ng/mL) after oral administration to rats at a dose of 3 mg/kg

| Time (h) | Male 7 | Male 8 | Male 9 | Mean | SD |
|---|---|---|---|---|---|
| 12 | 144.7 | 28.2 | 128.1 | 100.3 | 63.0 |
| 24 | 60.5 | 0.0 | 0.0 | ND | 0.0 |

The results in Table 3 show that after 12 hours, the mean amount of Compound 2 remaining in the blood was 100.3 ng/mL. The results at 24 hours were less consistent and the mean was not determined at this time. The $IC_{50}$ of Compound 2 in the whole blood eosinophil shape change assay is 2 nM (0.9 ng/ml) and is therefore ca. 111 times over the whole blood eosinophil shape change $IC_{50}$ at 12 hrs. The results therefore show that Compound 2 is suitable for oral administration to a patient, although the profile is not as favourable as that of Compound 1.

TABLE 4

Concentration of Compound 3 in blood (ng/mL) after oral administration to rats at a dose of 3 mg/kg

| Time (h) | Male 13 | Male 14 | Male 15 | Mean | SD |
|---|---|---|---|---|---|
| 0.25 | 835.8 | 1130.7 | 1337.2 | 1101.2 | 252.0 |
| 0.5 | 2056.6 | 2205.2 | 2487.5 | 2249.8 | 218.9 |
| 1 | 2487.6 | 3547.8 | 3393.7 | 3143.0 | 572.8 |
| 2 | 4320.6 | 3685.1 | 4221.0 | 4075.6 | 341.8 |
| 4 | 3132.0 | 2023.1 | 2053.8 | 2403.0 | 631.5 |
| 6 | 1333.7 | 995.0 | 1098.0 | 1142.2 | 173.6 |
| 8 | 1163.7 | 699.5 | 678.5 | 847.2 | 274.3 |
| 12 | 465.3 | 163.3 | 201.1 | 276.6 | 164.5 |
| 24 | 38.2 | 0.0 | 10.1 | 16.1 | 19.8 |

The results in Table 4 show that after 24 hours, the mean amount of Compound 3 remaining in the blood was 16.1 ng/mL. The $IC_{50}$ of Compound 1 in the whole blood eosinophil shape change assay is 6 nM (2.7 ng/ml) and is therefore ca. 6 times over the whole blood eosinophil shape change $IC_{50}$ at 24 hrs. The results therefore show that Compound 3 is particularly suitable for oral administration to a patient.

The results in Table 5 show that after 24 hours, the mean amount of Compound (A) remaining in the blood was 43.7 ng/mL. The $IC_{50}$ of Compound 1 in the whole blood eosinophil shape change assay is 103 nM (35.8 ng/ml) and is therefore ca. 1.2 times over the whole blood eosinophil shape change $IC_{50}$ at 24 hrs.

TABLE 5

Concentration of Compound (A) in blood (ng/mL) after oral administration to rats at a dose of 3 mg/kg

| Time (h) | Male 4 | Male 5 | Male 6 | Mean | Stdev |
|---|---|---|---|---|---|
| 0.25 | 139.1 | 153.9 | 68.3 | 120.4 | 45.8 |
| 0.5 | 425.6 | 388.4 | 256.3 | 356.8 | 89.0 |
| 1 | 875.2 | 923.2 | 538.8 | 779.1 | 209.5 |
| 2 | 1415.1 | 1309.0 | 1013.6 | 1245.9 | 208.1 |
| 4 | 923.1 | 820.5 | 827.0 | 856.9 | 57.5 |
| 6 | 404.3 | 514.8 | 432.6 | 450.6 | 57.4 |
| 8 | 305.6 | 521.9 | 235.5 | 354.3 | 149.3 |
| 24 | 51.8 | 79.2 | 0.0 | 43.7 | 40.2 |

TABLE 6

Concentration of Compound (B) in blood (ng/mL) after oral administration to rats at a dose of 3 mg/kg

| Time (h) | Male 31 | Male 32 | Male 33 | Mean | Stdev |
|---|---|---|---|---|---|
| 0.25 | 91.8 | 113.6 | 57.3 | 87.6 | 28.4 |
| 0.5 | 121.2 | 165.7 | 132.1 | 139.7 | 23.2 |
| 1 | 252.1 | 295.1 | 217.5 | 254.9 | 38.9 |
| 2 | 349.9 | 536.9 | 256.2 | 381.0 | 142.9 |
| 4 | 179.4 | 485.2 | 184.9 | 283.2 | 175.0 |
| 6 | 128.3 | 292.2 | 125.8 | 182.1 | 95.4 |
| 8 | 72.1 | 184.5 | 84.7 | 113.8 | 61.6 |
| 12 | 36.5 | 31.0 | 14.5 | 27.3 | 11.4 |
| 24 | 0 | 0 | 0 | 0 | 0 |

The results in Table 6 show that after 12 hours, the mean amount of Compound B remaining in the blood was 27.3 ng/mL. The $IC_{50}$ of Compound B in the whole blood eosinophil shape change assay is 8 nM (3.0 ng/ml) and is therefore ca. 9.1 times over the whole blood eosinophil shape change $IC_{50}$ at 12 hrs.

Figure 2:
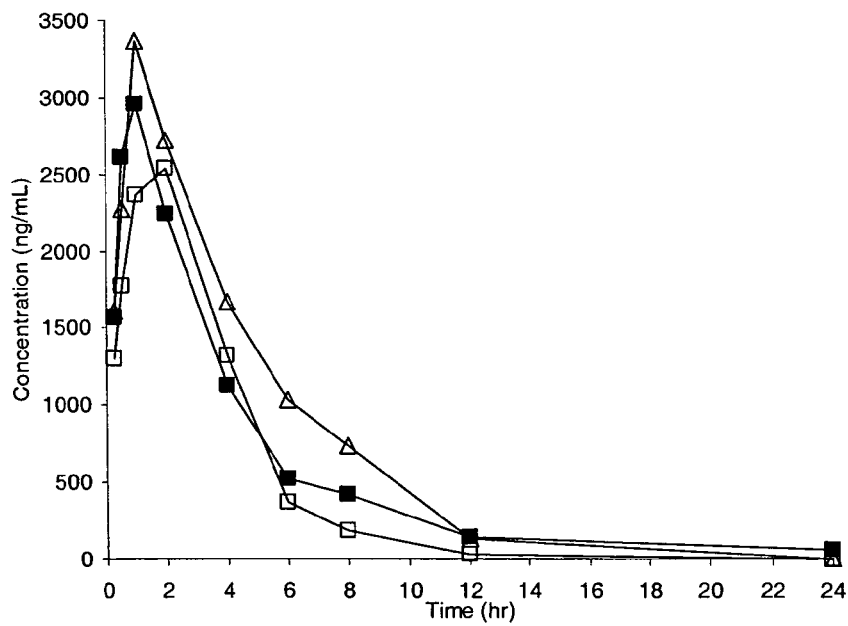
FIG. 2 is a plot of blood concentration of Compound 2 versus time for rats dosed orally with 3 mg/kg of Compound 2.
Figure 3:
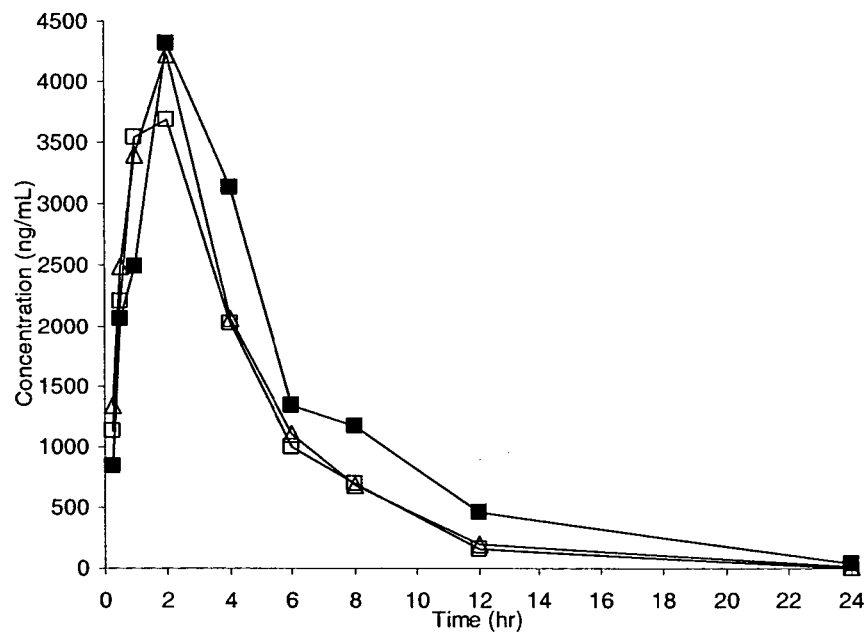
FIG. 3 is a plot of blood concentration of Compound 3 versus time for rats dosed orally with 3 mg/kg of Compound 3.
Figure 4:
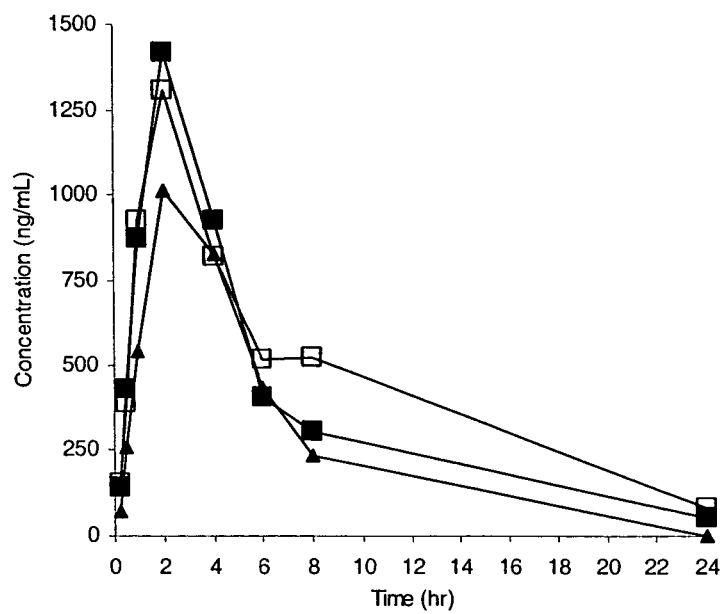
FIG. 4 is a plot of blood concentration of Comparator Compound A versus time for rats dosed orally with 3 mg/kg of Compound A.
Figure 5:
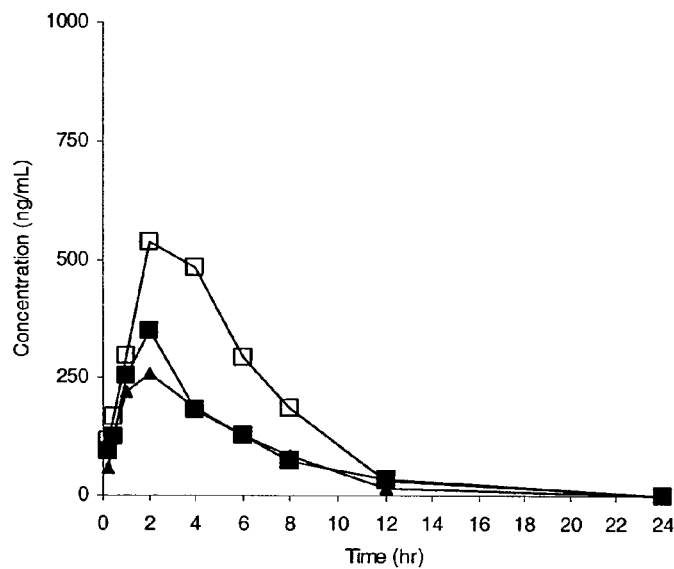
FIG. 5 is a plot of blood concentration of Comparator Compound B versus time for rats dosed orally with 3 mg/kg of Compound B.

FIGS. 1 to 5 are plots blood concentration of compound versus time for rats dosed orally with 3 mg/kg of Compounds 1, 2, 3, A and B respectively. They are therefore graphical representations of the data set out in Tables 2 to 6.

The values for $C_{max}$ (maximum blood concentration), $T_{max}$, (time at which $C_{max}$ occurs), $AUC_{inf}$ (area under curve to infinity) and $T_{1/2}$ (half life) taken from FIGS. 1 to 5 are set out in Tables 7 to 11 for Compounds 1, 2, 3, A and B respectively.

The values for $C_{max}$ and the $AUC_{inf}$ represent the exposure of a subject to an oral dose of the compound. It is therefore preferred that the figures for both $C_{max}$ and AUC should be as high as possible so that exposure to the compound is maximised.

TABLE 7

PK Parameters for 3 mg/kg Compound 1 p.o

| Parameter | Units | Male 4 | Male 5 | Male 6 | Mean |
|---|---|---|---|---|---|
| Cmax | ng/mL | 4331 | 3895 | 4263 | 4163 |
| Tmax | hours | 2 | 1 | 1 | 1.3 |
| AUCinf | ng/mL * hrs | 23809 | 14846 | 21731 | 19328 |
| T½ | hours | 4.11 | 3.07 | 4.59 | 3.6 |

TABLE 8

PK Parameters for 3 mg/kg Compound 2 p.o

| Parameter | Units | Male 7 | Male 8 | Male 9 | Mean |
|---|---|---|---|---|---|
| Cmax | ng/mL | 2958.0 | 2537.0 | 3366.0 | 2954 |
| Tmax | hours | 1.0 | 2.0 | 1.0 | 1.3 |
| AUCinf | ng/mL * hrs | 13153 | 10179 | 15677 | 11666 |
| T½ | hours | 6 | 2 | 2 | 3.7 |

TABLE 9

PK Parameters for 3 mg/kg Compound 3 p.o

| Parameter | Units | Male 13 | Male 14 | Male 15 | Mean |
|---|---|---|---|---|---|
| Cmax | ng/mL | 4321 | 3685 | 4221 | 4076 |
| Tmax | hours | 2 | 2 | 2 | 2.0 |
| AUCinf | ng/mL * hrs | 24379 | 17738 | 19110 | 21059 |
| T½ | hours | 3.26 | 2.26 | 2.62 | 2.8 |

TABLE 10

PK Parameters for 3 mg/kg Compound (A) p.o

| Parameter | Units | Male 4 | Male 5 | Male 6 | Mean |
|---|---|---|---|---|---|
| Cmax | ng/mL | 1415.1 | 1309.0 | 1013.6 | 1245.9 |
| Tmax | hours | 2.0 | 2.0 | 2.0 | 2.0 |
| AUCinf | ng/mL * hrs | 8570.4 | 10429.2 | 5473.9 | 8157.8 |
| T½ | hours | 6.1 | 6.1 | 2.2 | 4.8 |

TABLE 11

PK Parameters for 3 mg/kg Compound (B) p.o

| Parameter | Units | Male 4 | Male 5 | Male 6 | Mean |
|---|---|---|---|---|---|
| Cmax | ng/mL | 349.9 | 536.9 | 256.2 | 381.0 |
| Tmax | hours | 2.0 | 2.0 | 2.0 | 2.0 |
| AUCinf | ng/mL * hrs | 1831.4 | 3256.1 | 1505.1 | 2197.6 |
| T½ | hours | 3.41 | 1.80 | 1.86 | 2.4 |

From Tables 7 to 11 it can be seen that Compounds 1, 2 and 3 have mean $C_{max}$ values of 4163, 2954 and 4076 respectively. In contrast, the mean values for Compounds A and B are only 1245.9 and 381.0.

The $AUC_{inf}$ values for Compounds 1, 2 and 3 are 19238, 11666 and 21059, while those for Compounds A and B are 8157.8 and 2197.6.

Thus the figures for both $C_{max}$ and $AUC_{inf}$ are significantly higher for the compounds of the present invention than those for Comparator Compounds A and B. It is clear from these results that subjects dosed orally with Compounds A and B would have much lower exposure to the drug than subjects dosed orally with Compounds 1, 2 and 3.

The results from Examples 4 and 5 are summarised in Table 12, in which the Fold over $IC_{50}$ at 12 h is defined as the mean amount of compound remaining in the blood at 12 hours in ng/ml divided by the $IC_{50}$ of the compound in ng/ml. Similarly the fold over $IC_{50}$ at 24 h is defined as is defined as the mean amount of compound remaining in the blood at 24 hours in ng/ml divided by the $IC_{50}$ of the compound in ng/ml.

TABLE 12

| | Compound | | | | |
|---|---|---|---|---|---|
| | 1 | 2 | 3 | A | B |
| $IC_{50}$ (µmol) | 0.005 | 0.002 | 0.006 | 0.103 | 0.008 |
| $IC_{50}$ (ng/mL) | 2.2 | 0.9 | 2.7 | 35.8 | 3.0 |
| Fold over $IC_{50}$ at 12 h | 170 | 111 | 102 | ND | 9.1 |
| Fold over $IC_{50}$ at 24 h | 21 | ND | 6 | 1.2 | 0 |
| $C_{max}$ | 4163 | 2954 | 4076 | 1246 | 381 |
| $AUC_{inf}$ | 19328 | 11666 | 21059 | 8158 | 2198 |

Table 12 shows that Comparator Compound A has a higher $IC_{50}$ than Compounds 1, 2 and 3 and a lower value for fold over $IC_{50}$ at 24 hours than Compounds 1 and 3. The exposure of a subject to the drug after oral administration as indicated by $C_{max}$ and $AUC_{inf}$ is significantly lower for Compound A than for any of Compounds 1 to 3.

Compound B has an $IC_{50}$ value which is comparable to that of Compounds 1, 2 and 3. However, the fold over $IC_{50}$ at 12 and 24 hours is significantly less favourable than that of any of Compounds 1 to 3 and the exposure of a subject to the drug after oral administration as indicated by $C_{max}$ and $AUC_{inf}$ is significantly lower for Compound B than for any of Compounds 1 to 3.

Comparator Compounds A and B each have some properties which are comparable with those of Compounds 1, 2 and 3. However, taken as a whole, their properties are less favourable than those of the compounds of the invention.

Example 6

Evaluation of Compounds of General Formula (I) as Inhibitors of 13,14-dihydro-15-keto prostaglandin D2 (DK-PGD2)-Induced Blood Eosinophilia in Rats Protocol The test compound was dissolved in DMSO and diluted with water to give a final dosing volume of 2 ml/kg.

Female rats (175-250 g; UH colony) were dosed orally with test compound (or vehicle).

30 min after dosing all animals were anaesthetised with isoflurane.

Following induction of anaesthesia, animals receive an intracardiac injection of 10 µg $DK-PGD_2$ in 0.3 ml heparinised (10 U/ml) saline. Control animals received an injection of 0.3 ml heparinised saline.

60 min after the intracardiac injection, animals were injected with an overdose of pentobarbitone sodium and a blood sample was taken (into heparin) by cardiac puncture while the rat was anaesthetised but not dead.

An aliquot of blood (100 µl) was added to Turk's solution and the total leukocyte count determined with a haemocytometer.

A further aliquot of blood (500 µl) was mixed with an equal volume of 4% Dextran (mw 500,000) and the erythrocytes allowed to settle. A cytospin preparation was made from the resulting leukocyte rich fraction.

Cytospin preparations were fixed with methanol (5 min) and stained with May-Grunwald (5 min) and Giemsa (15 min) stains. Finally cytospins were washed in phosphate buffer (pH6.8) and air dried.

Differential leukocyte counts were obtained from the cytospin preparations.

Blood eosinophil numbers were determined from the total leukocyte count and the percentage eosinophils (differential count).

Experimental Design

Up to 12 animals were used in each experiment. Groups included:

Untreated controls $DK-PGD_2$-induced eosinophilia, vehicle treated animals (positive control)

$DK-PGD_2$-induced eosinophilia, Compound 1; doses of 0.0001, 0.001, 0.01 and 0.1 µg/kg p.o.

$DK-PGD_2$-induced eosinophilia, Compound 2; doses of 0.001, 0.01, 0.1 and 1.0 µg/kg p.o.

$DK-PGD_2$-induced eosinophilia, Compound 3; doses of 0.001, 0.01, 0.1 and 1.0 µg/kg p.o.

$DK-PGD_2$-induced eosinophilia, Compound A; doses of 0.01, 0.1 and 1.0 mg/kg p.o.

$DK-PGD_2$-induced eosinophilia, Compound A; doses of 0.001, 0.01, 0.1 and 1.0 mg/kg p.o.

Because it was impractical to generate sufficient data in any given experiment, data were obtained over a number of replicate experiments. Data from these replicate experiments were pooled, to provide at least 5 animals in each group and a dose-response curve fitted following a significance test (Mann Whitney) to determine whether or not $DK-PGD_2$ caused a significant increase in blood eosinophils (GraphPad, Prism). A difference between groups was taken to be significant when P<0.05. ED50 values were calculated from the dose-response curve.

Figure 6:
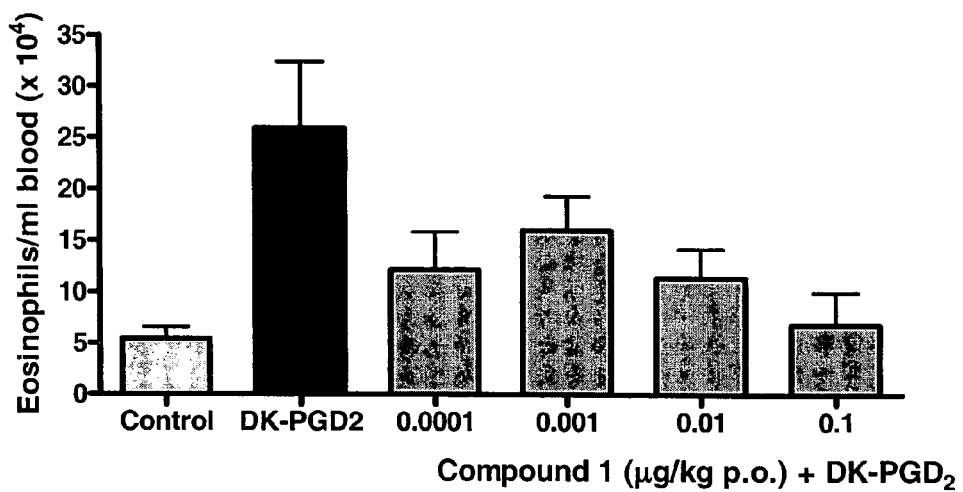
FIG. 6 shows the effect of doses of 0.0001, 0.001, 0.01 and 0.1 μg/kg of Compound 1 on DK-$PGD_2$ induced eosinophilia in rats.
Figure 7:
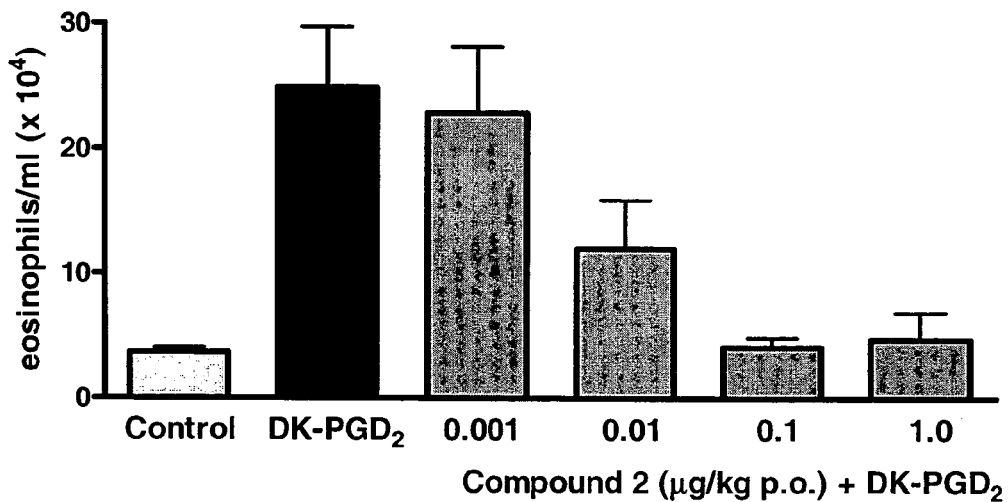
FIG. 7 shows the effect of doses of 0.001, 0.01, 0.1 and 1.0 μg/kg of Compound 2 on DK-$PGD_2$ induced eosinophilia in rats.
Figure 8:
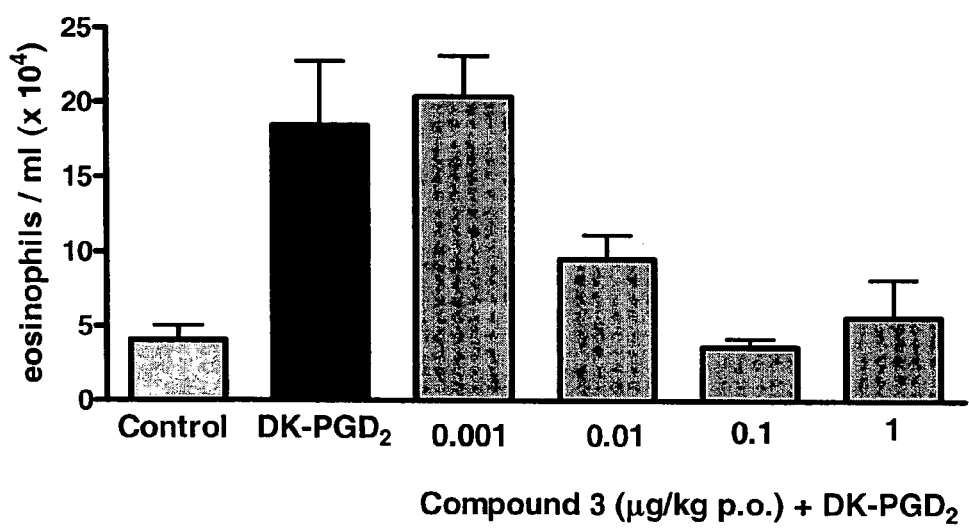
FIG. 8 shows the effect of doses of 0.001, 0.01, 0.1 and 1.0 μg/kg of Compound 3 on DK-$PGD_2$ induced eosinophilia in rats.
Figure 9:
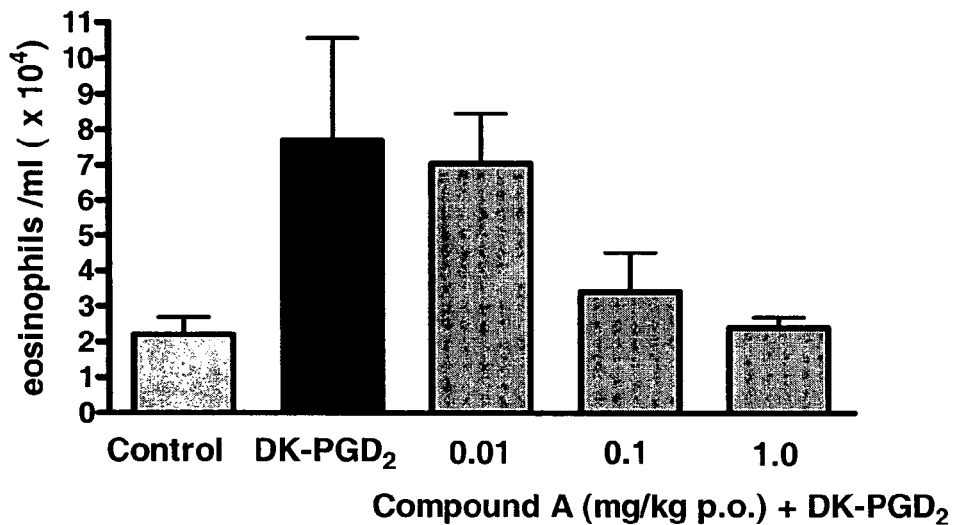
FIG. 9 shows the effect of doses of 0.01, 0.1 and 1.0 mg/kg of Compound A on DK-$PGD_2$ induced eosinophilia in rats.
Figure 10:
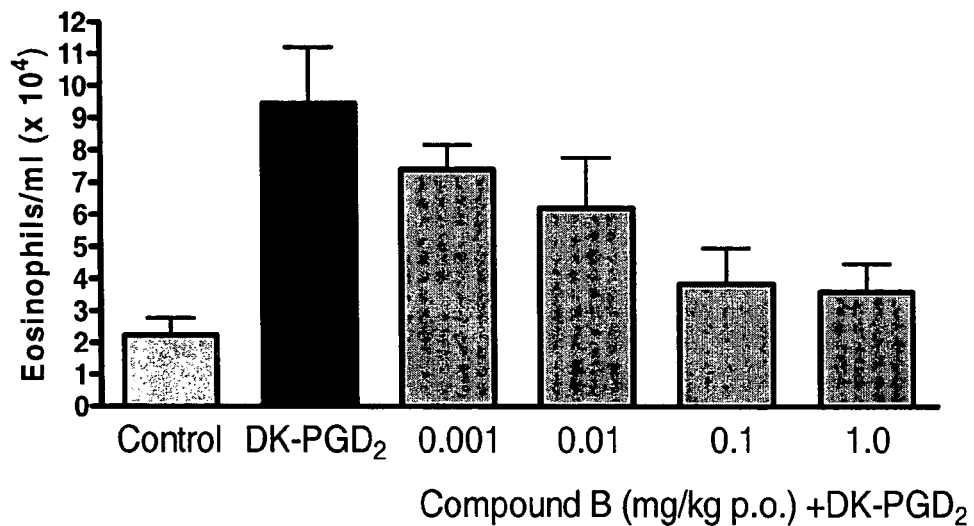
FIG. 10 shows the effect of doses of 0.001, 0.01, 0.1 and 1.0 mg/kg of Compound B on DK-$PGD_2$ induced eosinophilia in rats.

The results of these experiments are shown in FIGS. 6 to 10 and in Table 13 below.

TABLE 13

| | Compound | | | | |
|---|---|---|---|---|---|
| | 1 | 2 | 3 | A | B |
| Potency in inhibition of DK-PGD$_2$-induced blood eosinophilia (μg/ml) | 0.0025 | 0.010 | 0.010 | 37 | 17 |

It can be seen from Table 13 and FIGS. 6-10 that Compounds 1-3 are several thousand times more potent than Comparator Compounds A and B in inhibiting DK-PGD$_2$-induced blood eosinophilia in rats.

The invention claimed is:

1. A compound of general formula (I)

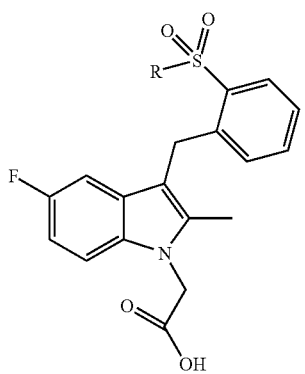

(I)

wherein R is phenyl optionally substituted with one or more halo substituents;
or a pharmaceutically acceptable salt, thereof.

2. A compound of general formula (II):

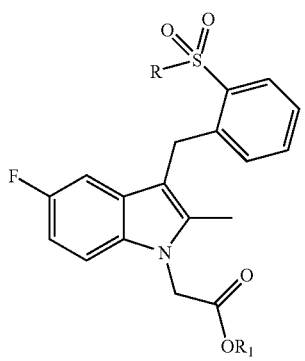

II wherein R is phenyl optionally substituted with one or more halo substituents; and
R$^1$ is C$_1$-C$_6$ alkyl, aryl, (CH$_2$)$_m$OC(=O)C$_1$-C$_6$alkyl, (CH$_2$)$_m$N(R$^{11}$)$_2$, or CH((CH$_2$)$_m$O(C=O)R$^{12}$)$_2$;
m is 1 or 2;
R$^{11}$ is hydrogen or methyl;
R$^{12}$ is C$_1$-C$_{18}$ alkyl.

3. A compound as claimed in claim 1 or claim 2, wherein the phenyl group R is unsubstituted or is substituted with a single halo substituent.

4. A compound as claimed in claim 3, wherein the halo substituent is fluoro or chloro.

5. A compound as claimed in claim 4, wherein the fluoro or chloro substituent is at the 4-position of the phenyl group R.

6. A compound selected from the group consisting of:
2-{5-Fluoro-2-methyl-3-[2-(phenylsulfonyl)benzyl]-1H-indol-1-yl}acetic acid;
2-{3-[2-(4-chlorophenylsulfony)benzyl]-5-fluoro-2-methyl-1H-indol-1-yl}acetic acid;
2-{5-Fluoro-3-[2-(4-fluorophenylsulfonyl)benzyl]-2-methyl-1H-indol-1-yl}acetic acid;
and the C$_1$-C$_6$ alkyl, aryl, (CH$_2$)$_m$OC(=O)C$_1$-C$_6$alkyl, (CH$_2$)$_m$N(R$^{11}$)$_2$, CH((CH$_2$)$_m$O(C=O)R$^{12}$)$_2$ esters thereof; wherein
m is 1 or 2;
R$^{11}$ is hydrogen or methyl; and
R$^{12}$ is C$_1$-C$_{18}$ alkyl.

7. A pharmaceutical composition comprising a compound as claimed in claim 1 or claim 2 together with a pharmaceutical excipient or carrier.

8. A composition as claimed in claim 7 formulated for oral, rectal, nasal, bronchial, topical, vaginal or parenteral administration.

9. A composition as claimed in claim 7 further comprising one or more additional active agents useful in the treatment of diseases and conditions mediated by PGD$_2$ or other agonists at the CRTH2 receptor.

10. A composition as claimed in claim 9, wherein the additional active agents are selected from the group consisting of:
other CRTH2 antagonists,
Suplatast tosylate,
β$_1$ to β$_4$ adrenoreceptor agonists, methylxanthanines, mast cell stabilisers, muscarinic receptor antagonists, antihistamines,
α$_1$ and α$_2$ adrenoreceptor agonists,
insulin-like growth factor (IGF-1) mimetics,
matrix metalloprotease (MMP) inhibitors,
modulators of chemokine receptor function,
antiviral agents, antisepsis compounds,
cardiovascular agents,
CNS agents,
Tryptase inhibitors,
Platelet activating factor (PAF) antagonists,
Interleukin converting enzyme (ICE) inhibitors,
IMPDH inhibitors,
Adhesion molecule inhibitors,
Cathepsins,
MAP kinase inhibitors,
Glucose-6-phosphonate dehydrogenase inhibitors,
Kinin-B$_1$ and B$_2$ receptor antagonists,
Anti-gout agents,
Xantine oxidase inhibitors,
Uricosuric agents,
Growth hormone secretagogues,
Transforming growth factor beta (TGFβ),
Platelet-derived growth factor (PGDF),
Fibroblast growth factor,
Granulocyte macrophage colony stimulating factor (GM-CSF),
Capsaicin,
Tachykinin NK$_1$ and NK$_3$ receptor antagonists,
Elastase inhibitors,
Induced nitric oxide synthase inhibitors (iNOS), Osteoporosis agents,
anticholinergic agents,
leukotriene antagonists,
leukotriene biosynthesis inhibitors,
Phosphdiesterase inhibitors,
anti-IgE antibody therapies,
anti-infectives,
anti-fungals,
immunosuppressants,
antiproliferative/antineoplastic drugs,
antitumour antibiotics,
antimitotic agents, cytostatic agents, oestrogen receptor down regulators, LHRH antagonists or agonists, progestogens, aromatase inhibitors,
agents which inhibit cancer cell invasion,
inhibitors of growth factor function, farnesyl transferase inhibitors, tyrosine kinase inhibitors, serine or threonine kinase inhibitors,
antiangiogenic agents,
vascular damaging agents,
antisense therapies,
gene therapy agents,
immunotherapy agents,
corticosteroids, hyaluronic acids,
drugs which promote Th1 cytokine response,
other antagonists of $PGD_2$ acting at other receptors,
inhibitors of phoshodiesterase type 4,
drugs that modulate cytokine production, inhibitors of other TNF isoforms, non-selective COX-1/COX-2 inhibitors, COX-2 inhibitors, low dose methotrexate, lefunomide, ciclesonide, hydroxychloroquine, d-penicillamine, auranofin, parenteral or oral gold,
drugs that modulate the activity of Th2 cytokines IL-4 and IL-5,
PPAR-γ agonists,
anti-RSV antibodies, and agents that may be used to treat rhinovirus infection.

* * * * *